(12) United States Patent
Soucaille et al.

(10) Patent No.: US 9,121,041 B2
(45) Date of Patent: *Sep. 1, 2015

(54) METHOD FOR THE PREPARATION OF DIOLS

(75) Inventors: Philippe Soucaille, Deyme (FR); Cédric Boisart, Gerzat (FR)

(73) Assignee: METABOLIC EXPLORER, Saint Beauzire (FR)

( * ) Notice: Subject to any disclaimer, the term of this patent is extended or adjusted under 35 U.S.C. 154(b) by 454 days.

This patent is subject to a terminal disclaimer.

(21) Appl. No.: 13/169,703

(22) Filed: Jun. 27, 2011

(65) Prior Publication Data

US 2011/0294178 A1 Dec. 1, 2011

Related U.S. Application Data

(63) Continuation-in-part of application No. PCT/EP2009/067994, filed on Dec. 29, 2009.

(60) Provisional application No. 61/361,459, filed on Jul. 5, 2009, provisional application No. 61/141,699, filed on Dec. 31, 2008.

(30) Foreign Application Priority Data

Dec. 31, 2008 (EP) ..................................... 08173129

(51) Int. Cl.

| C12N 9/10 | (2006.01) |
|---|---|
| C12N 9/02 | (2006.01) |
| C12N 9/88 | (2006.01) |
| C12N 15/00 | (2006.01) |
| C12N 1/20 | (2006.01) |
| C12P 7/04 | (2006.01) |
| C07H 21/04 | (2006.01) |
| C12P 7/18 | (2006.01) |
| C12N 9/04 | (2006.01) |
| C12N 15/70 | (2006.01) |

(52) U.S. Cl.
CPC ................. *C12P 7/18* (2013.01); *C12N 9/0006* (2013.01); *C12N 9/1096* (2013.01); *C12N 9/88* (2013.01); *C12N 15/70* (2013.01); *C12P 7/04* (2013.01)

(58) Field of Classification Search
CPC ........ C12N 9/1096; C12N 15/63; C12N 9/88; C12N 9/0006; C12N 15/70; C12P 7/42; C12P 7/04; C12P 7/18
See application file for complete search history.

(56) References Cited

U.S. PATENT DOCUMENTS

| 7,267,972 | B2 | 9/2007 | Sarcabal et al. |
|---|---|---|---|
| 7,582,460 | B2 | 9/2009 | Maier et al. |
| 7,745,195 | B2 | 6/2010 | Chateau et al. |
| 2007/0072279 | A1 | 3/2007 | Meynial-Salles et al. |
| 2007/0087403 | A1 | 4/2007 | Bestel-Corre et al. |
| 2007/0259411 | A1* | 11/2007 | Bramucci et al. ............ 435/160 |
| 2008/0085558 | A1 | 4/2008 | Soucaille et al. |
| 2008/0233617 | A1 | 9/2008 | Figge et al. |
| 2008/0286840 | A1 | 11/2008 | Figge et al. |
| 2008/0311632 | A1 | 12/2008 | Figge et al. |
| 2009/0029424 | A1 | 1/2009 | Bestel-Corre et al. |
| 2009/0155867 | A1 | 6/2009 | Soucaille |
| 2009/0325245 | A1 | 12/2009 | Soucaille et al. |
| 2010/0086982 | A1 | 4/2010 | Soucaille |
| 2010/0137655 | A1 | 6/2010 | Soucaille |

FOREIGN PATENT DOCUMENTS

| EP | 0 620 853 | 10/1994 |
|---|---|---|
| EP | 0 931 833 | 7/1999 |
| EP | 1496111 | 1/2005 |
| WO | 9635796 | 11/1996 |
| WO | 0112833 | 2/2001 |
| WO | 2004033646 | 4/2004 |
| WO | 2004/076659 | 9/2004 |
| WO | 2005/047498 | 5/2005 |
| WO | 2005/073364 | 8/2005 |
| WO | 2005/111202 | 11/2005 |
| WO | 2006/082252 | 8/2006 |
| WO | 2006/082254 | 8/2006 |
| WO | 2007/017710 | 2/2007 |
| WO | 2007/077041 | 7/2007 |
| WO | 2007/141316 | 12/2007 |
| WO | 2007/144346 | 12/2007 |

(Continued)

OTHER PUBLICATIONS

Atsumi et al. Non-fermentative pathways for synthesis of branched-chain higher alcohols as biofuels. Nature. Jan. 3, 2008;451(7174):86-9. doi: 10.1038/nature06450.*
Atsumi et al. Engineering the isobutanol biosynthetic pathway in *Escherichia coli* by comparison of three aldehyde reductase/alcohol dehydrogenase genes. Appl Microbiol Biotechnol. Jan. 2010;85(3):651-7. doi: 10.1007/s00253-009-2085-6. Epub Jul. 16, 2009.*
Branden et al. Introduction to Protein Structure, Garland Publishing Inc., New York, p. 247, 1991.*
International Search Report of PCT/EP2009/067994, dated Apr. 6, 2010.
Anderson; "Growth Requirements of Virus-Resistant Mutants of *Escherichia coli* Strain "B""; Department of Biology; 1946; Proc. Natl. Acad Sci; USA; pp. 120-128.
Ballou et al; "The Synthesis and Properties of Hydroxypyruvic Acid Phosphate" 1956; J. Am Chem Soc; vol. 78; pp. 3718-3720.
Datsenko et al.; "One-Step Inactivation of Chromosomal Genes in *Escherichia coli* K-12 Using PCR Products"; PNAS; 2000; vol. 97; No. 12; pp. 6640-6645.
Harrington et al.; "Balanced Branching in Transcription Termination"; PNAS; 2001; vol. 98; No. 9; pp. 5019-5024.
Korte et al.; "Alpha-Hydroxyalkyliden-Lacton-Umlagerung in Waessriger Salzsaeure"; 1959; Chem Ber; pp. 877-883.

(Continued)

*Primary Examiner* — Yong Pak
(74) *Attorney, Agent, or Firm* — Miles & Stockbridge P.C.

(57) ABSTRACT

The present invention concerns a new method for the biological preparation of a diol comprising culturing a microorganism genetically modified for the bioproduction of an aliphatic diol, wherein the microorganism comprises a metabolic pathway for the decarboxylation of a hydroxy-2-keto-aliphatic acid metabolite with an enzyme having a 2-keto acid decarboxylase activity, the product obtained from said decarboxylation step being further reduced into the corresponding aliphatic diol, and wherein the microorganism is genetically modified for the improved production of said hydroxy-2-keto-aliphatic acid metabolite.
The invention also concerns a modified microorganism for the production of an aliphatic diol.

8 Claims, 5 Drawing Sheets

(56) References Cited

FOREIGN PATENT DOCUMENTS

Figure 1:
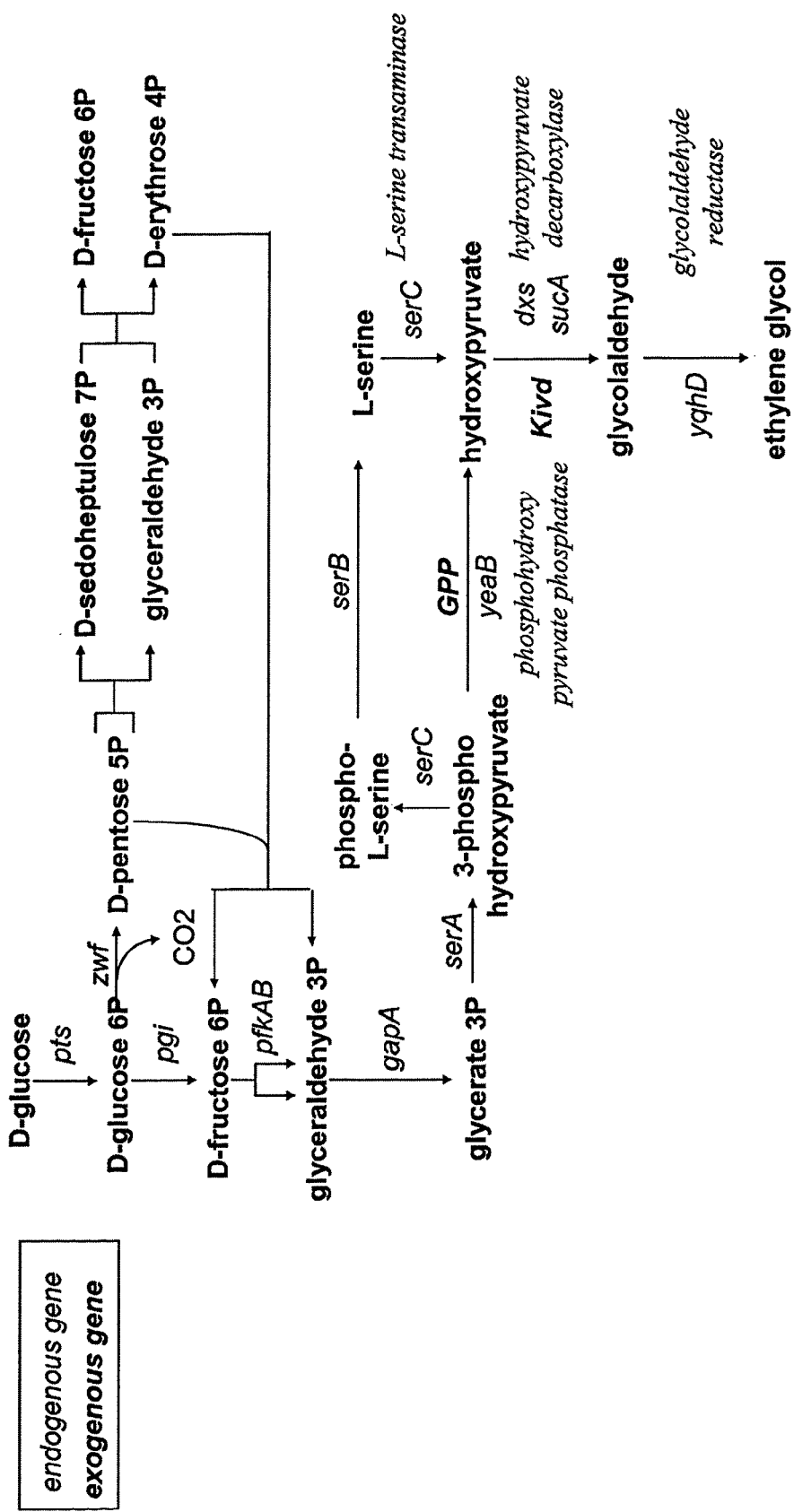

| WO | 2008/040387 | 4/2008 |
|----|-------------|--------|
| WO | 2008/052595 | 5/2008 |
| WO | 2008/052973 | 5/2008 |
| WO | 2008115840 | 9/2008 |

OTHER PUBLICATIONS

Lane et al.; "2-Keto-4-Hydroxybutyrate. Synthesis, Chemical Properties, and as a Substrate for Lactate Dehydrogenase of Rabbit Muscle"; 1969; Biochemistry; pp. 2958-2966.

Lee et al.; "Global Analyses of Transcriptomes and Proteomes of a Parent Strain and an L-Threonine-Overproducing Mutant Strain"; Journal of Bacteriology; 2003; vol. 185; No. 18; pp. 5442-5451.

Lerner et al.; "Low Number Plasmids for Regulated Low-Level Expression of Cloned Genes in Escherichia coli With Blue/White Insert Screening Capability"; Nucleic Acids Research; vol. 18; No. 15; 1990; p. 4631.

Li et al.; "Enhanced Activity of yqhD Oxidoreductase in Synthesis of 1,3-Propanediol by Error-Prone PCR"; Progress in Natural Science 18; 2008; pp. 1519-1524.

Liebl et al.; "Requirement of Chelating Compounds for the Growth of Corynebacterium Glutamicum in Synthetic Media"; Appl Microbiol Biotechnol; 1989; 32:205-210.

Norrander et al.; "Construction of Improved M13 Vectors Using Oligodeoxynucleotide-Directed Mutagenesis"; Gene; 1983; pp. 101-106.

Paul et al.; "Transposition Des Dihydro-2.5 Furannes En Dihydro-2.3 Furannes.—Application a La Preparation De L'Hydroxy-4 Butanal"; Bulletin De La Societe Chimique De France' 1950; pp. 668-671.

Riedel et al.; "Characterization of the Phosphoenolpyruvate Carboxykinase Gene From Corynebacterium Glutamicum and Significance of the Enzyme for Growth and Amino Acid Production"; J. Mol. Microbiol. Biotechnol.; 2001; 3(4): 573-583.

Schaefer et al.; "Automated Sampling Device for Monitoring Intracellular Metabolite Dynamics"; Analytical Biochemistry; 270; 1999; pp. 88-96.

Miller; "A Short Course in Bacterial Genetics: A Laboratory Manual and Handbook for Escherichia coli and Related Bacteria"; Cold Spring Harbor Laboratory Press, Cold Spring Harbor, New York; 1992 (Book).

* cited by examiner

| Gene | Organism | Accession number |
|---|---|---|
| Pdc2 | Arabidopsis thaliana | NC_003076 REGION: complement(22327913..22329987) |
| Pdc3 | Arabidopsis thaliana | NC_003076 REGION: complement(132318..134861) |
| Pdc | Clostridium acetobutylicum | NC_001988 REGION: 24954..26618 |
| aceA | Escherichia coli | NC_000913 REGION: 4215132..4216436 |
| aceB | Escherichia coli | NC_000913 REGION: 4213501..4215102 |
| aceK | Escherichia coli | NC_000913 REGION: 4216619..4218355 |
| arcA | Escherichia coli | NC_000913 REGION: complement(4637613..4638329) |
| asd | Escherichia coli | NC_000913 REGION: complement(3571798..3572901) |
| cysE | Escherichia coli | NC_000913 REGION: complement(3779764..3780585) |
| dapA | Escherichia coli | NC_000913 REGION: complement(2596904..2597782) |
| dkgA | Escherichia coli | NC_000913 REGION: 3154645..3155472 |
| dkgB | Escherichia coli | NC_000913 REGION: 229167..229970 |
| fucO | Escherichia coli | NC_000913 REGION: complement(2929887..2931038) |
| galP | Escherichia coli | NC_000913 REGION: 3086306..3087700 |
| gdhA | Escherichia coli | NC_000913 REGION: 1840395..1841738 |
| gltA | Escherichia coli | NC_000913 REGION: complement(752408..753691) |
| gltB | Escherichia coli | NC_000913 REGION: 3352654..3357207 |
| glyA | Escherichia coli | NC_000913 REGION: complement(2682276..2683529) |
| gpmA | Escherichia coli | NC_000913 REGION: complement(786066..786818) |
| gpmB | Escherichia coli | NC_000913 REGION: 4631820..4632467 |
| icd | Escherichia coli | NC_000913 REGION: 1194346..1195596 |
| lrp | Escherichia coli | NC_000913 REGION: 931818..932312 |
| maeA | Escherichia coli | NC_000913 REGION: complement(1551996..1553693) |
| maeB | Escherichia coli | NC_000913 REGION: complement(2574120..2576399) |
| metA | Escherichia coli | NC_000913 REGION: 4212303..4213232 |
| pckA | Escherichia coli | NC_000913 REGION: 3530840..3532462 |
| ppc | Escherichia coli | NC_000913 REGION: complement(4148470..4151121) |
| ppsA | Escherichia coli | NC_000913 REGION: complement(1782758..1785136) |
| pykA | Escherichia coli | NC_000913 REGION: 1935673..1937115 |
| pykF | Escherichia coli | NC_000913 REGION: 1753722..1755134 |
| sdaA | Escherichia coli | NC_000913 REGION: 1894956..1896320 |
| sdaB | Escherichia coli | NC_000913 REGION: 2927598..2928965 |
| serA | Escherichia coli | NC_000913 REGION: complement(3055200..3056432) |
| serC | Escherichia coli | NC_000913 REGION: 956876..957964 |
| sucA | Escherichia coli | NC_000913 REGION: 757929..760730 |
| sucB | Escherichia coli | NC_000913 REGION: 760745..761962 |
| sucC | Escherichia coli | NC_000913 REGION: 762237..763403 |
| sucD | Escherichia coli | NC_000913 REGION: 763403..764272 |
| thrA | Escherichia coli | NC_000913 REGION: 337..2799 |
| thrB | Escherichia coli | NC_000913 REGION: 2801..3733 |
| thrC | Escherichia coli | NC_000913 REGION: 3734..5020 |
| trpA | Escherichia coli | NC_000913 REGION: complement(1314440..1315246) |
| trpB | Escherichia coli | NC_000913 REGION: complement(1315246..1316439) |
| yqhD | Escherichia coli | NC_000913 REGION: 3153377..3154540 |

Fig 4-1

| Kivd | Lactococcus lactis | AJ746364 |
|---|---|---|
| Aro10 | Pichia stipitis | NC_009046 REGION: complement(1053281..1055152) |
| Pdc1 | Pichia stipitis | NC_009068 REGION: 1765715..1767920 |
| Pdc2 | Pichia stipitis | NC_009068 REGION: complement(285510..287347) |
| ADH1 | Saccharomyces cerevisiae | NC_001147 REGION: complement(159548..160594) |
| ADH2 | Saccharomyces cerevisiae | NC_001145 REGION: complement(873290..874336) |
| Aro10 | Saccharomyces cerevisiae | NC_001136 REGION: 1234210..1236117 |
| Pdc1 | Saccharomyces cerevisiae | NC_001144 REGION: complement(232391..234082) |
| Pdc5 | Saccharomyces cerevisiae | NC_001144 REGION: 410724..412415 |
| Pdc6 | Saccharomyces cerevisiae | NC_001139 REGION: complement(651294..652985) |
| Thi3 | Saccharomyces cerevisiae | NC_001136 REGION: complement(310642..312471) |
| pdc | Zymomonas mobilis | NC_006526 REGION: complement(1373405..1375111) |
| yeaB | Escherichia coli | NC_000913 REGION: 1894194..1894772 |
| aldA | Escherichia coli | NC_000913 REGION: 1486256..1487695 |
| aldB | Escherichia coli | NC_000913 REGION: complement(3754534..3752996) |
| aao | Rhodococcus opacus | NC_012522 REGION: complement(1799119..1800723) |

Fig 4-2

METHOD FOR THE PREPARATION OF DIOLS

CROSS-REFERENCE TO RELATED APPLICATIONS

This Non-Provisional patent application claims priority to U.S. Patent Application No. 61/361,459, filed Jul. 5, 2010. This Non-Provisional patent application is a continuation-in-part of PCT/EP2009/067994, filed Dec. 29, 2009, which claims priority to European Application No. 08173129.1, filed Dec. 31, 2008 and U.S. Patent Application No. 61/141,699, filed Dec. 31, 2008. Each application cited is hereby incorporated by reference in its entirety.

BACKGROUND

1. Field of the Invention

The present invention concerns a new method for the biological preparation of a diol comprising culturing a microorganism genetically modified for the bioproduction of an aliphatic diol, wherein the microorganism comprises a metabolic pathway for the decarboxylation of a hydroxy-2-keto-aliphatic acid metabolite with two enzymes: an enzyme having a 2-keto acid decarboxylase activity and an enzyme having a hydroxy aldehyde reductase activity. The invention also concerns a modified microorganism for the production of an aliphatic diol.

2. Description of Related Art

Fermentative production of diols by culturing microorganism producing such diols are known in the art, including fermentative production with microorganisms genetically modified for an improved production of the diols. Production of such diols is described, inter alia, in the following documents: WO1996/035796, WO2001/012833, WO2004/033646, U.S. Pat. No. 7,267,972. In particular, production of 1,3-propanediol has already been described, involving vitamin B12-dependent enzymes, thereby making the production process very expensive.

There is an ongoing need for alternative solutions of modified microorganisms, to either or both produce diols from renewable sources of carbon and have potential improvement in the production of the diols, particularly with vitamin B12-independent pathways. These technical improvements may be on the overall yield of product being produced based on the energy necessary for such production and eventually, the level of impurities and by-products to be specifically controlled for isolation of the product and its marketing and further use.

SUMMARY OF THE INVENTION

The present invention concerns a microorganism genetically modified for the bioproduction of an aliphatic diol, wherein the microorganism comprises a metabolic pathway for the decarboxylation of a hydroxy-2-keto-aliphatic acid metabolite with an enzyme having a 2-keto acid decarboxylase activity, the product obtained from said decarboxylation step being further reduced into the corresponding aliphatic diol with an enzyme having a hydroxy aldehyde reductase activity, and wherein the microorganism is genetically modified for the improved production of said hydroxy-2-keto-aliphatic acid metabolite.

The microorganism of the invention is generally selected among the group consisting of a bacterium, yeast or a fungus. Preferentially, the microorganism is selected among Enterobacteriaceae, Clostridiaceae, Bacillaceae, Streptomycetaceae and Corynebacteriaceae.

According to a first embodiment the microorganism comprises an endogenous gene coding for a 2-keto acid decarboxylase activity. It is preferably selected among *Saccharomyces cerevisiae* (Pdc1, Pdc5, Pdc6, Aro10, Thi3); *Lactococcus lactis* (Kivd); *Clostridium acetobutylicum* (Pdc); *Arabidopsis thaliana* (Pdc2, Pdc3); *Pichia stipitis* (Pdc1, Pdc2, Aro10); *Zymomonas mobilis* (Pdc); *Mycobacterium tuberculosis*. This microorganism having endogenous 2-keto acid decarboxylase activity can be further modified to enhance expression of the endogenous gene coding for the 2-keto acid decarboxylase.

According to another embodiment of the invention, the microorganism does not comprise an endogenous gene coding for a 2-keto acid decarboxylase. Such microorganism lacking endogenous 2-keto acid decarboxylase is preferably selected among *Escherichia coli* or *Corynebacterium glutamicum* or *Bacillus subtilis*. For such microorganisms, the microorganism of the invention comprises a heterologous gene coding for a 2-ketoacid decarboxylase.

According to another embodiment the microorganism comprises an endogenous gene coding for a hydroxy aldehyde reductase activity. It is preferably selected among *Escherichia coli* (yqhD, fucO, dkgA, dkgB); *Saccharomyces cerevisiae* (ADH1, ADH2, ... ); and all organisms having at least one enzyme having aldehyde reductase activity or alcohol dehydrogenase activity. This microorganism having endogenous hydroxy aldehyde reductase activity can be further modified to enhance expression of the endogenous gene coding for the hydroxy aldehyde reductase.

The aliphatic diol produced with the microorganism of the invention is an aliphatic diol having a linear or branched alkyle chain comprising from 2 to 6 carbon atoms, preferably 2, 3 or 4 carbon atoms.

In a preferred embodiment, the aliphatic diol is ethyleneglycol and the hydroxy-2-keto-aliphatic acid metabolite is hydroxypyruvate.

In another preferred embodiment, the aliphatic diol is 1,3-propanediol and the hydroxy-2-keto-aliphatic acid metabolite is 4-hydroxy-2-ketobutyrate.

In another preferred embodiment, the aliphatic diol is 1,4-butanediol and the hydroxy-2-keto-aliphatic acid metabolite is 5-hydroxy-2-ketopentanoate.

The present invention also concerns a method for the bioproduction of an aliphatic diol, comprising the steps of
 culturing a microorganism of the invention as described above and below on an appropriate culture medium comprising a source of carbon and
 recovering the aliphatic diol from the culture medium.
According to preferred embodiment of the invention, the diol is further purified.

DETAILED DESCRIPTION OF A PREFERRED EMBODIMENT

Microorganisms

The microorganism of the invention is a microorganism being genetically modified or genetically engineered. This means, according to the usual meaning of these terms, that the microorganism of the invention is not found in nature and is modified either by introduction or by deletion of new genetic elements. It can also be transformed by forcing the development and evolution of new metabolic pathways in combining directed mutagenesis and evolution under specific selection pressure (see for instance WO 2004/076659).

According to the invention, the term "microorganism" designates a bacterium, yeast or a fungus. Preferentially, the microorganism is selected among Enterobacteriaceae, Clostridiaceae, Bacillaceae, Streptomycetaceae and Corynebacteriaceae. More preferentially the microorganism is a species of *Escherichia, Clostridium, Bacillus, Klebsiella, Pantoea, Salmonella* or *Corynebacterium*. Even more preferentially the microorganism is either the species *Escherichia coli* or *Corynebacterium glutamicum* or *Clostridium acetobutylicum* or *Bacillus subtilis*.

A microorganism can express exogenous genes if these genes are introduced into the microorganism with all the elements allowing their expression in the host microorganism. Transforming microorganisms with exogenous DNA is a routine task for the man skilled in the art.

Exogenous genes can be integrated into the host genome, or be expressed extrachromosomally by plasmids or vectors. Different types of plasmids are known by the man skilled in the art, which differ with respect to their origin of replication and their copy number in the cell.

Important elements for controlling the expression of genes are promoters. In a preferred embodiment of the invention, genes may be expressed using promoters with different strength, which may be inducible. These promoters may be homologous or heterologous. The man skilled in the art knows how to choose the promoters that are the most convenient, for example promoters Ptrc, Ptac, Plac or the lambda promoter a are widely used.

In specific embodiments, endogenous genes can also be modified to modulate their expression and/or activity, by introducing either mutations in the coding sequence to modify the gene product or by introducing heterologous sequences in addition or in replacement of the endogenous regulatory elements. Modulation of an endogenous gene can go both ways: upregulating and/or enhancing the activity of the gene product on the one hand, or down regulating and/or lowering the activity of the endogenous gene product on the other hand.

The term 'attenuation of a gene' according to the invention denotes the partial or complete suppression of the expression of a gene, which is then said to be 'attenuated'. This suppression of expression can be either an inhibition of the expression of the gene, a deletion of all or part of the promoter region necessary for the gene expression, a deletion in the coding region of the gene, or the replacement of the wild-type promoter by a weaker natural or synthetic promoter. Preferentially, the attenuation of a gene is essentially the complete deletion of that gene, which can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

In other embodiments of the invention, endogenous sequences may also be knocked out or deleted, to favour the new metabolic pathway.

All techniques for transforming the microorganisms, and regulatory elements used for enhancing production of the protein of the invention are well known in the art and available in the literature, including applicant's own patent applications on modification of biosynthesis pathways in various microorganisms, including WO 2008/052973, WO 2008/052595, WO 2008/040387, WO 2007/144346, WO 2007/141316, WO 2007/077041, WO 2007/017710, WO 2006/082254, WO 2006/082252, WO 2005/111202, WO 2005/073364, WO 2005/047498, WO 2004/076659, the content of which is incorporated herein by reference.

Genes and Enzymatic Activities

In the description of the present invention, enzymatic activities are also designated by reference to the genes coding for the enzymes having such activity. Except mentioned otherwise, genes and proteins are generally identified using the denominations of genes from *Escherichia coli*. However, use of these denominations has a more general meaning according to the invention and covers all the corresponding genes and proteins in other organisms, more particularly microorganisms, functional homologues, functional variants and functional fragments of said genes and proteins.

Genes being identified in the present application are listed in FIG. 4 with their accession number.

Using the references of the IUBMB Enzyme Nomenclature for known enzymatic activities, those skilled in the art are able to determine the same enzymatic activities in other organisms, bacterial strains, yeasts, fungi, etc. This routine work is advantageously done using consensus sequences that can be determined by carrying out sequence alignments with proteins derived from other microorganisms.

Methods for the determination of the percentage of homology between two protein sequences are known from the man skilled in the art. For example, it can be made after alignment of the sequences by using the software CLUSTALW available on the European Bioinformatics Institute website with the default parameters indicated on the website. From the alignment, calculation of the percentage of identity can be made easily by recording the number of identical residues at the same position compared to the total number of residues. Alternatively, automatic calculation can be made by using for example the BLAST programs available on the National Center for Biotechnology Information website with the default parameters indicated on the website.

PFAM (protein families database of alignments and hidden Markov models; that can be used on the Wellcome Trust Sanger Institute website) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; that can be used on the National Center for Biotechnology Information website are obtained by comparing protein sequences from 66 fully sequenced genomes representing 30 major phylogenic lines. Each COG is defined from at least three lines, which permits the identification of former conserved domains.

A protein sharing homology with the cited protein may be obtained from other microorganisms or may be a variant or a functional fragment of a natural protein.

The term "functional variant or functional fragment" means that the amino-acid sequence of the polypeptide may not be strictly limited to the sequence observed in nature, but may contain additional amino-acids. The term "functional fragment" means that the sequence of the polypeptide may include less amino-acid than the original sequence but still enough amino-acids to confer the enzymatic activity of the original sequence of reference. It is well known in the art that a polypeptide can be modified by substitution, insertion, deletion and/or addition of one or more amino-acids while retaining its enzymatic activity. For example, substitution of one amino-acid at a given position by a chemically equivalent amino-acid that does not affect the functional properties of a protein are common. For the purpose of the present invention, substitutions are defined as exchanges within one of the following groups:

Small aliphatic, non-polar or slightly polar residues: Ala, Ser, Thr, Pro, Gly

Polar, negatively charged residues and their amides: Asp, Asn, Glu, Gln

Polar, positively charged residues: H is, Arg, Lys

Large aliphatic, non-polar residues: Met, Leu, Ile, Val, Cys

Large aromatic residues: Phe, Tyr, Trp.

Changes that result in the substitution of one negatively charged residue for another (such as glutamic acid for aspartic acid) or one positively charged residue for another (such as lysine for arginine) can be expected to produce a functionally equivalent product.

The positions where the amino-acids are modified and the number of amino-acids subject to modification in the amino-acid sequence are not particularly limited. The man skilled in the art is able to recognize the modifications that can be introduced without affecting the activity of the protein. For example, modifications in the N- or C-terminal portion of a protein may be expected not to alter the activity of a protein under certain circumstances.

The term "variant" refers to polypeptides submitted to modifications such as defined above while still retaining the original enzymatic activity.

The terms "encoding" or "coding" refer to the process by which a polynucleotide, through the mechanisms of transcription and translation, produces an amino-acid sequence. This process is allowed by the genetic code, which is the relation between the sequence of bases in DNA and the sequence of amino-acids in proteins. One major feature of the genetic code is that it is degenerate, meaning that one amino-acid can be coded by more than one triplet of bases (one "codon"). The direct consequence is that the same amino-acid sequence can be encoded by different polynucleotides. It is well known from the man skilled in the art that the use of codons can vary according to the organisms. Among the codons coding for the same amino-acid, some can be used preferentially by a given microorganism. It can thus be of interest to design a polynucleotide adapted to the codon usage of a particular microorganism in order to optimize the expression of the corresponding protein in this organism.

In some instance, genes or enzymes may be designated by the name of the activity. In some other instances, the designation by "activity" may mean a combination of two or more enzymes having in combination the desired activity. In such case, each enzyme in the combination may be encoded by distinct genes under control of different regulatory elements or a combination of genes under control of the same operon.

Genes coding for a 2-keto acid decarboxylase activity are well known in the art, including Pdc genes from various species, and more particularly the Pdc1, Pdc5, Pdc6, Aro10 and Thi3 genes from *Saccharomyces cerevisiae*, kivD gene from *Lactococcus lactis*; pdc gene from *Clostridium acetobutylicum*; Pdc2 and Pdc3 genes from *Arabidopsis thaliana*; Pdc1, Pdc2 and Aro10 genes from *Pichia stipitis*; pdc gene from *Zymomonas mobilis*. The first subunit of the 2-ketoglutarate decarboxylase complex, encoded by the gene sucA from *Escherichia coli*, also possesses 2-keto acid decarboxylase activity, as well as the enzyme encoded by the gene dxs of *Escherichia coli*. Functional homologues, functional variants and functional fragments of said genes and proteins are encompassed by the definition.

Genes coding for a hydroxy aldehyde reductase activity are also well known in the art, including the yqhD, fucO, dkgA, dkgB genes from *Escherichia coli* and the ADH1 and ADH2 genes from *Saccharomyces cerevisiae*. Functional homologues, functional variants and functional fragments of said genes and proteins are encompassed by the definition.

Fermentative Production

The present invention also concerns the fermentative production of an aliphatic diol, comprising the steps of culturing a microorganism on an appropriate culture medium comprising a source of carbon and recovering the aliphatic diol from the culture medium.

The fermentation is generally conducted in fermenters with an appropriate culture medium adapted to the microorganism being used, containing at least one simple carbon source, and if necessary co-substrates.

An 'appropriate culture medium' designates a medium (e.g., a sterile, liquid media) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like.

As an example of known culture mediums for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As another example of a culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

The term 'carbon source' or 'carbon substrate' or 'source of carbon' according to the present invention denotes any source of carbon that can be used by those skilled in the art to support the normal growth of a micro-organism, including hexoses (such as glucose, galactose or lactose), pentoses, monosaccharides, disaccharides, oligosaccharides (such as sucrose, cellobiose or maltose), molasses, starch or its derivatives, hemicelluloses, glycerol and combinations thereof. An especially preferred simple carbon source is glucose. Another preferred simple carbon source is sucrose.

In some embodiments of the invention, the culture medium comprises a carbon source being a by-product of another process using biomass as starting material, or eventually, the product of mechanical and/or chemical and/or enzymatic, and in such instance in vitro or in vivo, degradation of biomass, such as degradation of cellulose.

The microorganism of the invention is advantageously elected and/or modified to use the source of carbon as sole source of carbon to grow on the culture medium.

Microorganisms selected to grow on a specific source of carbon are known in the art, as well as modifications to be introduced in a microorganism to allow it to grow on said specific source of carbon.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

Recovering the aliphatic diol from the culture medium is a routine task for a man skilled in the art.

In one aspect of the invention, the recovered aliphatic diol is further purified.

Methods for recovering a diol from a culture medium and its purification are known in the art and disclosed, inter alia in the following documents: PCT/EP2008/063287 filed on Oct. 3, 2008 and PCT/EP2007/063068 filed on Nov. 30, 2007.

Specific Embodiments

Other embodiments of the invention will be described below. The microorganisms are modified both to favor the production of the hydroxy-2-keto-aliphatic acid metabolite and the transformation into the corresponding aliphatic diol of the product obtained from the decarboxylation step of the same hydroxy-2-keto-aliphatic acid metabolite.

The description below is made by reference to *E. coli*, which microorganism is lacking endogenous 2-keto acid decarboxylase activity. Therefore, a heterologous gene coding for said activity is introduced into the microorganism.

Modifications of the microorganism to optimise the pathway for producing the hydroxy-2-keto-aliphatic acid metabolite and to transform the product obtained from the decarboxylation step of the same hydroxy-2-keto-aliphatic acid metabolite into the aliphatic diol is also made based on the known metabolic pathways and endogenous genes of *E. coli*. However, the man skilled in the art can use similar strategies to introduce or delete corresponding genes in other microorganisms with known genes and pathways.

I. Preparation of Ethylene Glycol

The biosynthesis pathway for the production of ethylene glycol according to the invention comprises three enzymatic reactions starting with transformation of the 3-phosphohydroxypyruvate precursor (precursor for serine). First a phosphatase activity allows conversion of phosphohydroxypyruvate into hydroxypyruvate. Hydroxypyruvate is then transformed into glycolaldehyde with a 2-keto acid decarboxylase activity. Finally, a hydroxy aldehyde reductase activity allows the conversion of glycolaldehyde into ethylene glycol. Another pathway for the production of ethylene glycol starts from L-serine as precursor. First a transaminase or an amino acid oxidase activity allows conversion of serine into hydroxypyruvate. The next two steps are similar to the first pathway described above.

The global biosynthesis pathway is represented in FIG. 1.

The present invention provides a method for the fermentative production of ethylene glycol, its derivatives or precursors, comprising: culturing a microorganism, particularly a bacterium, in an appropriate culture medium comprising a source of carbon and recovering ethylene glycol from the culture medium.

In a preferred embodiment, the method is performed with a microorganism, particularly a bacterium, which contains at least one gene encoding a polypeptide with 2-keto acid decarboxylase activity and one gene encoding a polypeptide with hydroxy aldehyde reductase activity. Those genes can be exogenous or endogenous, and can be expressed chromosomally or extrachromosomally.

In a further embodiment of the invention, the method is performed with a microorganism, particularly a bacterium, in which the availability of the intermediate 3-phosphoglycerate is increased. Preferably, the increase is achieved by attenuating the level of expression of genes encoding phosphoglycerate mutases, in particular one or both genes gpmA and pgmI. This can be done by replacing the wild-type promoter of these genes by a weaker promoter, or by the use of an element destabilizing the corresponding messenger RNA or the protein. If needed, complete attenuation of the genes can also be achieved by the deletion of the corresponding DNA sequences. The invention is also related to the microorganism used in this particular embodiment of the invention, i.e. a microorganism, particularly a bacterium presenting an increased availability of 3-phosphoglycerate, in particular a microorganism, preferentially a bacterium, in which the expression of the genes coding for phosphoglycerate mutases is attenuated, preferably the expression of one or both genes gpmA and pgmI.

In another embodiment, the method is performed with a microorganism, particularly a bacterium, in which flux into the serine biosynthesis pathway is stimulated. This can be achieved by increasing the level of expression of 3-phosphoglycerate dehydrogenase and/or phosphoserine aminotransferase, encoded by the serA and serC genes, respectively. Increasing the level of expression of the 3-phosphoglycerate dehydrogenase and/or phosphoserine aminotransferase can be accomplished by introducing artificial promoters that drive the expression of the serA and/or serC genes, by increasing the number of copies in the cell or by introducing mutations into the serA and/or serC genes that increase the activity of the corresponding proteins. The expression of the serA gene can also be increased by replacing the wild type lrp gene (encoding the leucine-responsive regulatory protein) by an lrp mutated allele (such as the lrp-1 allele corresponding to a GLU114ASP substitution in the lrp protein) leading to the constitutive activation of the transcription of the serA gene. The invention is also related to the microorganism, particularly a bacterium, used in this particular embodiment of the invention.

In a particular embodiment of the invention mutations can be introduced into the serA gene that reduce the sensitivity of the SerA protein to the feed-back inhibitor serine (feed-back desensitized alleles) and thus permit an increased activity in the presence of serine. Examples of desensitized alleles, i.e. feed-back insensitive alleles, have been described in EP 0 931 833 (Ajinomoto) or EP 0 620 853 (Wacker).

In another embodiment the method is performed with a microorganism, particularly a bacterium, in which flux into the hydroxypyruvate biosynthesis pathway is stimulated. This result can be achieved by increasing the level of expression of serine transaminase or serine oxidase (for the pathway starting from serine as precursor), or by increasing the expression of 3-phosphohydroxypyruvate phosphatase. Increasing the level of expression of serine oxidase can be accomplished by introducing and overexpressing the gene coding for L-amino acid oxidase from *R. opacus*, or by introducing mutations into the gene that increase the activity of the corresponding protein. An increase in the expression of serine transaminase can be accomplished by introducing artificial promoters that drive the expression of the serC gene of *E. coli*, by increasing the number of copies in the cell or by introducing mutations into the serC gene that increase the activity of the corresponding protein. An increase of the expression of 3-phosphohydroxypyruvate phosphatase can be accomplished by introducing artificial promoters that drive the expression of the yeaB gene or serB gene of *E. coli*, by increasing the number of copies in the cell or by introducing mutations into the yeaB gene or the serB gene that increase the activity of the corresponding proteins. An increase of the expression of 3-phosphohydroxypyruvate phosphatase can also be accomplished by introducing and overexpressing the gene GPP2 from *S. cerevisiae*, or by introducing mutations into the GPP2 gene that increase the activity of the corresponding protein. The invention is also related to the microorganism, particularly a bacterium, used in this particular embodiment of the invention.

In a further embodiment of the invention, the microorganism, particularly a bacterium, is modified to present an attenuated level of serine conversion to other compounds than ethylene glycol. This result may be achieved by attenuating the level of serine consuming enzymes like serine deaminases (encoded by sdaA and sdaB and tdcG), serine transacetylase (encoded by cysE), tryptophan synthase (encoded by trpAB) or serine hydroxymethyltransferase (encoded by glyA). These genes can be attenuated by replacing the natural promoter by a lower strength promoter or by elements destabilizing the corresponding messenger RNA or the protein. If needed, complete attenuation of the gene can also be achieved by a deletion of the corresponding DNA sequence. The invention is also related to the microorganism, particularly a bacterium, used in this particular embodiment of the invention.

In a further embodiment of the invention, the microorganism, particularly a bacterium, is modified to present an attenuated level of hydroxypyruvate conversion to other compounds than glycolaldehyde. This result may be achieved by attenuating the level of hydroxypyruvate consuming enzymes like hydroxypyruvate reductase (encoded by ghrA) or hydroxypyruvate isomerase (encoded by hyi). These genes can be attenuated by replacing the natural promoter by a lower strength promoter or by elements destabilizing the corresponding messenger RNA or the protein. If needed, complete attenuation of the gene can also be achieved by a deletion of the corresponding DNA sequence. The invention is also related to the microorganism, particularly a bacterium, used in this particular embodiment of the invention.

In a further embodiment of the invention, the microorganism, particularly a bacterium, is modified to present an attenuated level of glycolaldehyde conversion to other compounds than ethylene glycol This may be achieved by attenuating the level of glycolaldehyde consuming enzymes like hydroxythreonine aldolase (encoded by ltaE) or glycolaldehyde dehydrogenase (encoded by aldA, aldB). Attenuation of these genes can be done by replacing the natural promoter by a lower strength promoter or by elements destabilizing the corresponding messenger RNA or the protein. If needed, complete attenuation of the gene can also be achieved by a deletion of the corresponding DNA sequence. The invention is also related to the microorganism, particularly a bacterium, used in this particular embodiment of the invention.

In one aspect of the invention, the efficiency of sugar import is increased, either by using a sugar import system not relying on phosphoenolpyruvate (PEP) as phosphordonor like galP that is known to transport glucose, or by providing more phosphoenolpyruvate (PEP) to the sugar-phosphotransferase system. Various means exist that may be used to increase the availability of PEP in a microorganism. In particular, this can be accomplished by attenuating the reaction PEP→pyruvate. Preferentially, at least one gene selected among pykA and pykF, encoding pyruvate kinase, is attenuated in said strain in order to obtain this result. Another way to increase the availability of PEP is to favour the reaction pyruvate→PEP. This can be accomplished by increasing the activity of phosphoenolpyruvate synthase which catalyzes the above reaction. This enzyme is encoded by the ppsA gene. Therefore, in the microorganism, the expression of the ppsA gene is preferentially increased. Both modifications can be present in the microorganism simultaneously.

II. Preparation of 1,3-propanediol

The biosynthesis pathway for the production of 1,3-propanediol according to the invention comprises three enzymatic reactions starting with transformation of the L-homoserine precursor (obtained from L-aspartate). First a homoserine transaminase or a homoserine oxidase activity allows conversion of L-homoserine into 4-hydroxy-2-ketobutyrate. A second 2-keto acid decarboxylase activity allows conversion of 4-hydroxy-2-ketobutyrate into 3-hydroxypropionaldehyde. 3-hydroxypropionaldehyde is then converted into 1,3-propanediol with a hydroxy aldehyde reductase activity.

Figure 2:
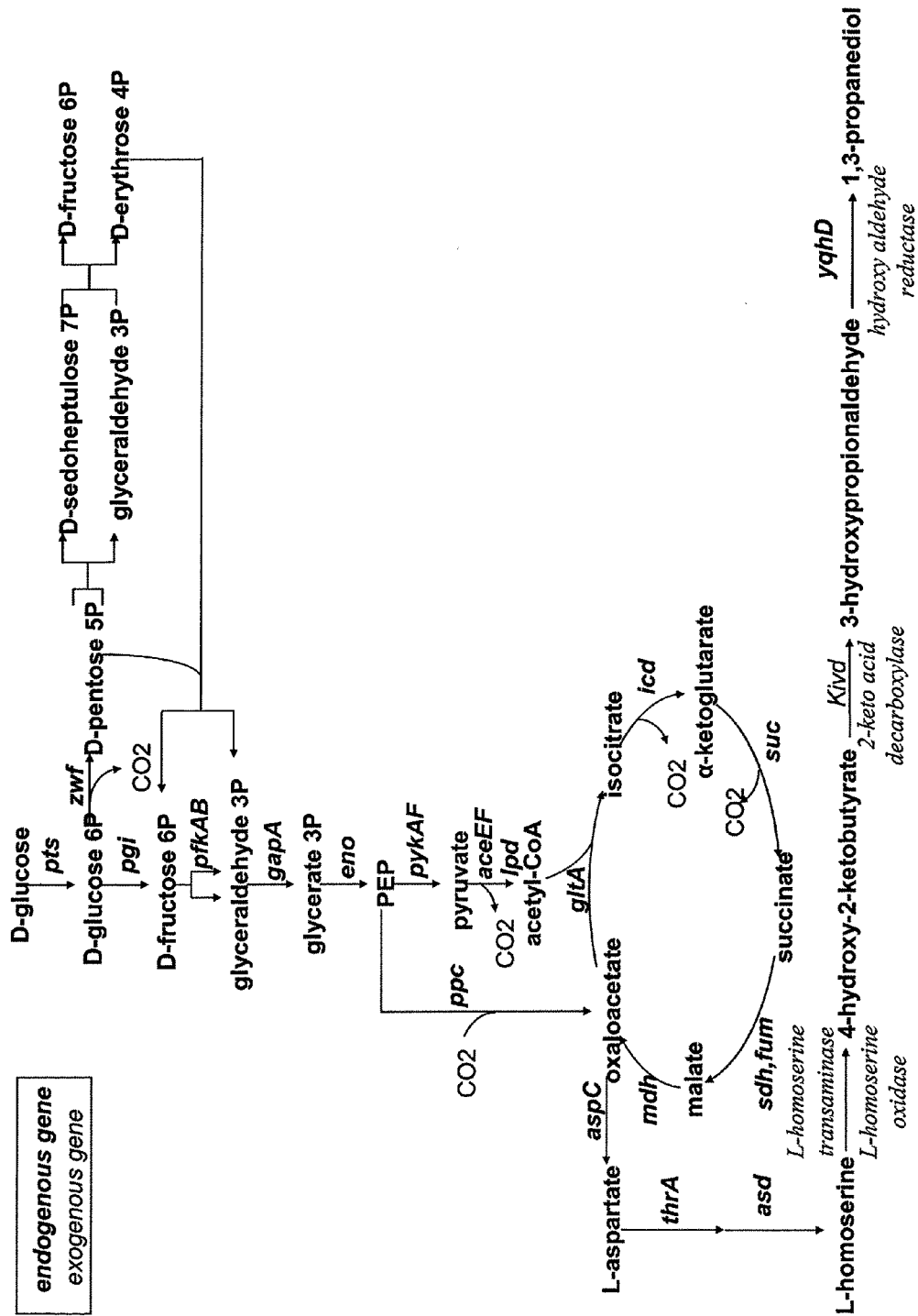

The global biosynthesis pathway is represented in FIG. 2.

The present invention provides a method for the fermentative production of 1,3-propanediol, its derivatives or precursors, comprising: culturing a microorganism, particularly a bacterium, in an appropriate culture medium comprising a source of carbon and recovering 1,3-propanediol from the culture medium.

In a preferred embodiment, the method is performed with a microorganism, particularly a bacterium, which contains at least one gene encoding a polypeptide with 2-keto acid decarboxylase activity and one gene encoding a polypeptide with hydroxy aldehyde reductase activity. Those genes can be exogenous or endogenous, and can be expressed chromosomally or extrachromosomally.

In another embodiment, the method is performed with a microorganism, particularly a bacterium, whose flux in the oxaloacetate biosynthesis pathway is stimulated; this result can be achieved by increasing the level of expression of phosphoenolpyruvate carboxylase, encoded by the ppc gene. Increasing the expression of phosphoenolpyruvate carboxylase can be accomplished by introducing artificial promoters that drive the expression of the ppc gene, by increasing the number of copies in the cell or by introducing mutations into the ppc gene that increase the activity of the corresponding protein. The availability of the intermediate product oxaloacetate can also be increased by attenuating the level of expression of genes coding for phosphoenolpyruvate carboxykinase and/or malic enzymes, encoded by the pckA and/or maeA and/or maeB genes, respectively. This can be done by replacing the wild-type promoter of these genes by a weaker promoter, or by the use of an element destabilizing the corresponding messenger RNA or the protein. If needed, complete attenuation of the genes can also be achieved by the deletion of the corresponding DNA sequences. The invention is also related to the microorganism, particularly a bacterium, used in this particular embodiment of the invention, i.e. a microorganism, particularly a bacterium, presenting an increased availability of the oxaloacetate.

In another embodiment, the method is performed with a microorganism, particularly a bacterium, in which flux into the homoserine biosynthesis pathway is stimulated. This can be achieved by increasing the expression of aspartokinase and homoserine dehydrogenase and/or aspartate semialdehyde dehydrogenase, encoded by the thrA and asd genes, respectively. Increasing the expression of aspartokinase and homoserine dehydrogenase and/or aspartate semialdehyde dehydrogenase can be accomplished by introducing artificial promoters that drive the expression of the thrA and/or asd genes, by increasing the number of copies in the cell or by introducing mutations into the thrA and/or asd genes that increase the activity of the corresponding proteins. The invention is also related to the microorganism, particularly a bacterium, used in this particular embodiment of the invention.

In a particular embodiment of the invention mutations can be introduced into the thrA gene that reduce its sensitivity to the feed-back inhibitor threonine (feed-back desensitized alleles) and thus permit an increased activity in the presence of threonine.

In another embodiment, the method is performed with a microorganism, particularly a bacterium, in which flux into the 4-hydroxy-2-ketobutyrate biosynthesis pathway is stimulated. This result can be achieved by increasing the expression of homoserine transaminase or homoserine oxidase. Increasing the expression of homoserine oxidase can be accomplished by introducing and overexpressing the gene coding for L-amino acid oxidase from *R. opacus*, or by introducing mutations into the gene that increase the activity of the corresponding protein. Increasing the level of expression of homoserine transaminase can be accomplished by introducing artificial promoters that drive the expression of the serC gene of *E. coli*, by increasing the number of copies in the cell or by introducing mutations into the serC gene that increase the activity of the corresponding protein. The invention is also related to the microorganism, particularly a bacterium, used in this particular embodiment of the invention.

In a further embodiment of the invention, the microorganism, particularly a bacterium, is modified to present an attenuated level of homoserine conversion to other compounds than 1,3-propanediol. This result may be achieved by attenuating the level of homoserine consuming enzymes like homoserine kinase and threonine synthase (encoded by thrB and thrC), homoserine O-transsuccinylase (encoded by metA) or dihydrodipicolinate synthase (encoded by dapA). These genes can be attenuated by replacing the natural promoter by a weaker promoter or by elements destabilizing the corresponding messenger RNA or protein. If needed, complete attenuation of the gene can also be achieved by the deletion of the corresponding DNA sequence. The invention is also related to the microorganism, particularly a bacterium, used in this particular embodiment of the invention.

In a further embodiment of the invention, the microorganism, particularly a bacterium, is modified to present an attenuated level of 3-hydroxypropionaldehyde conversion to other compounds than 1,3-propanediol. This may be achieved by attenuating the level of 3-hydroxypropionaldehyde consuming enzymes like 3-hydroxypropionaldehyde dehydrogenase (encoded by aldA, aldB). These genes can be attenuated by replacing the natural promoter by a weaker promoter or by elements destabilizing the corresponding messenger RNA or the protein. If needed, complete attenuation of the gene can also be achieved by the deletion of the corresponding DNA sequence. The invention is also related to the microorganism, particularly a bacterium, used in this particular embodiment of the invention.

In one aspect of the invention, the efficiency of the sugar import is increased, either by using a sugar import system not relying on phosphoenolpyruvate (PEP) as phosphordonor such as the one encoded by galP that is known to transport glucose, or by providing more phosphoenolpyruvate (PEP) to the sugar-phosphotransferase system. Various means exist that may be used to increase the availability of PEP in a microorganism. In particular, this may be accomplished by attenuating the reaction PEP→pyruvate. Preferentially, at least one gene selected among pykA and pykF, encoding pyruvate kinase, is attenuated in said strain in order to obtain this result. Another way to increase the availability of PEP is to favour the reaction pyruvate→PEP. This can be accomplished by increasing the activity of phosphoenolpyruvate synthase which catalyzes the above reaction. This enzyme is encoded by the ppsA gene. Therefore, in the microorganism, the expression of the ppsA gene is preferentially increased. Both modifications can be present in the microorganism simultaneously.

III. Preparation of 1,4-butanediol

The biosynthesis pathway for the production of 1,4-butanediol according to the invention comprises five enzymatic reactions starting with transformation of the 2-ketoglutarate precursor (metabolite of the Krebs cycle).

A first activity, 4-oxoglutaryl-CoA synthetase, allows conversion of 2-ketoglutarate into 4-oxoglutaryl-CoA. This compound is then converted into 5-hydroxy-2-ketopentanoate with the combinations of two activities, first aldehyde dehydrogenase then alcohol dehydrogenase both encoded by the gene adhE2 of *Clostridium acetobutylicum* or adhE of *Escherichia coli*. 2-keto acid decarboxylase activity allows then the conversion of 5-hydroxy-2-oxopentanoate into 4-hydroxybutyraldehyde, which is further converted into 1,4-butanediol relying on hydroxy aldehyde reductase activity.

Figure 3:
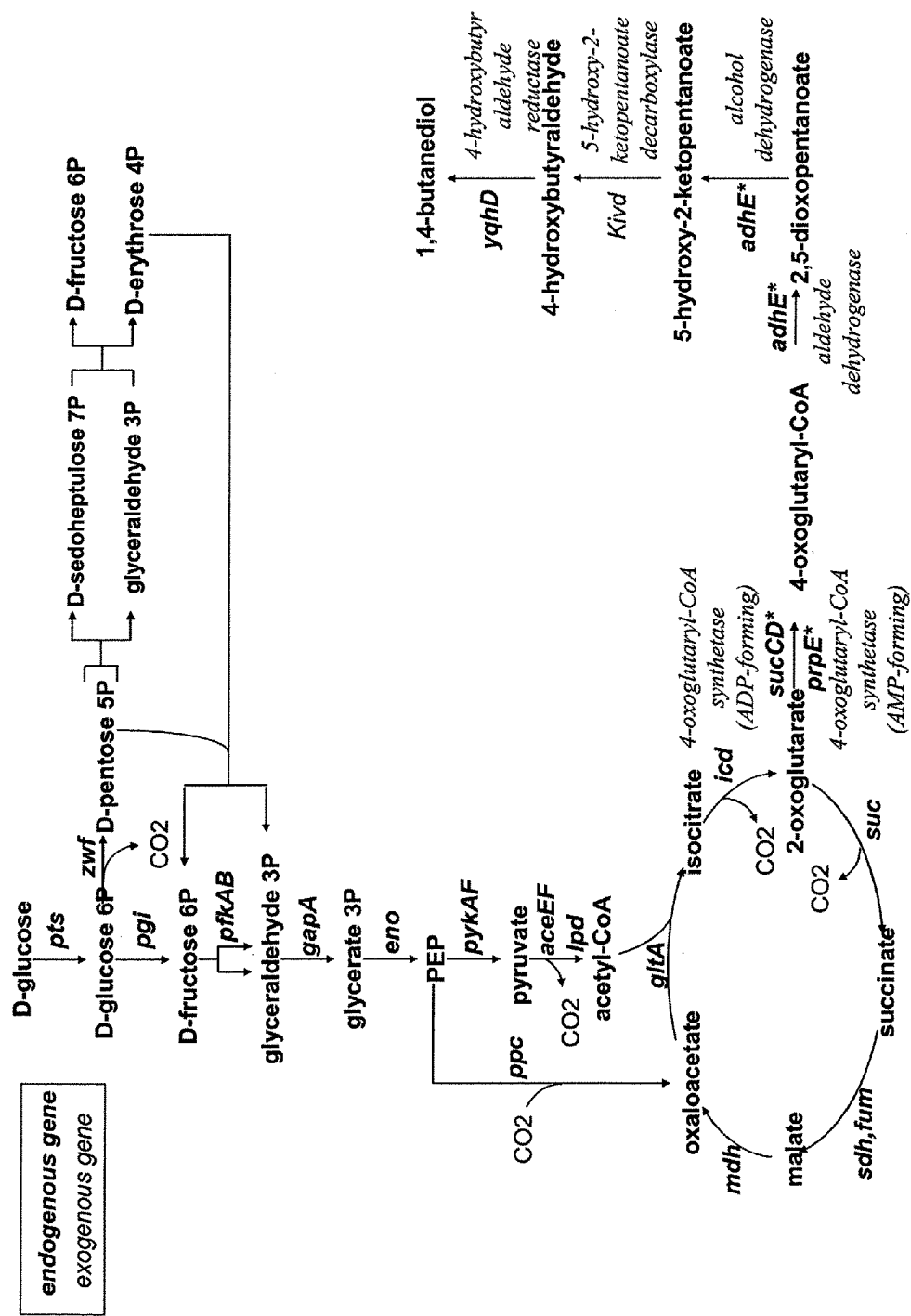

The global biosynthesis pathway is represented on FIG. 3.

The present invention provides a method for the fermentative production of 1,4-butanediol, its derivatives or precursors, comprising: culturing a microorganism, particularly a bacterium, in an appropriate culture medium comprising a source of carbon and recovering 1,4-butanediol from the culture medium.

In a preferred embodiment, the method is performed with a microorganism, particularly a bacterium, which contains at least one gene encoding a polypeptide with 2-keto acid decarboxylase activity and one gene encoding a polypeptide with hydroxy aldehyde reductase activity. Those genes can be exogenous or endogenous, and can be expressed chromosomally or extrachromosomally.

In another embodiment, the method is performed with a microorganism, particularly a bacterium, in which flux into the oxaloacetate biosynthesis pathway is stimulated (entry of the Krebs cycle). This can be achieved by increasing the expression of phosphoenolpyruvate carboxylase, encoded by the ppc gene. Increasing the expression of phosphoenolpyruvate carboxylase can be accomplished by introducing artificial promoters that drive the expression of the ppc gene, by increasing the number of copies in the cell or by introducing mutations into the ppc gene that increase the activity of the corresponding protein. Availability of the intermediate product oxaloacetate can also be increased by attenuating the level of expression of genes coding for phosphoenolpyruvate carboxykinase and/or malic enzymes, encoded by the pckA and/or maeA and/or maeB genes, respectively. This can be done by replacing the wild-type promoter of these genes by a weaker promoter, or by the use of an element destabilizing the corresponding messenger RNA or the protein. If needed, complete attenuation of the genes can also be achieved by the deletion of the corresponding DNA sequences. The invention is also related to the microorganism, particularly a bacterium, used in this particular embodiment of the invention, i.e. a microorganism, particularly a bacterium, presenting an increased availability of 2-ketoglutarate.

In another embodiment, the method is performed with a microorganism, particularly a bacterium, in which flux into the 2-ketoglutarate biosynthesis pathway is stimulated. This can be achieved by increasing the expression of citrate synthase and/or isocitrate dehydrogenase, encoded by the gltA and icd genes, respectively. Increasing the expression of citrate synthase and/or isocitrate dehydrogenase can be accomplished by introducing artificial promoters that drive the expression of the gltA and/or icd genes, by increasing the number of copies in the cell or by introducing mutations into the gltA and/or icd genes that increase the activity of the corresponding proteins. Isocitrate dehydrogenase activity is modulated by phosphorylation or dephosphorylation, reactions that are catalyzed by AceK. Phosphorylation reduces the activity of Icd and dephosphorylation reactivates the Icd enzyme. The activity of the Icd enzyme may therefore also be controlled by introducing mutant aceK genes that have reduced kinase activity or increased phosphatase activity compared to the wild type AceK enzyme. The level of AceK activity can also be decreased by attenuating the expression of the aceK gene. This can be done by replacing the wild-type promoter of the gene by a weaker promoter, or by the use of an element destabilizing the corresponding messenger RNA or the protein. If needed, complete attenuation of the gene can also be achieved by the deletion of the corresponding DNA sequence. Availability of the intermediate 2-ketoglutarate can also be increased by attenuating the expression of genes coding for 2-ketoglutarate decarboxylase or succinyl-CoA synthetase and/or isocitrate lyase or malate synthase, encoded by the sucAB or sucCD and/or aceA or aceB genes, respectively. This can be done by replacing the wild-type promoter of these genes by a weaker promoter, or by the use of an element destabilizing the corresponding messenger RNA or the protein. The flux in the Krebs cycle can also be increased by alleviating the repression of ArcA (encoded by the arcA gene) that represses Krebs cycle encoding genes. The invention is also related to the microorganism, particularly a bacterium, used in this particular embodiment of the invention, i.e. a microorganism, particularly a bacterium, presenting an increased availability of the 2-ketoglutarate.

In another embodiment, the method is performed with a microorganism, particularly a bacterium, in which flux into the 5-hydroxy-2-ketopentanoate biosynthesis pathway is stimulated. This can be achieved by increasing the expression of the 4-oxoglutaryl-CoA synthetase (AMP-forming, such as encoded by the prpE gene, or ADP-forming such as encoded by the sucC and sucD genes) and/or the aldehyde reductase/alcohol dehydrogenase. The invention is also related to the microorganism, particularly a bacterium, used in this particular embodiment of the invention.

In a further embodiment of the invention, the microorganism, particularly a bacterium, is modified to present an attenuated level of 2-ketoglutarate conversion to other compounds than 1,4-butanediol; This may be achieved by attenuating the level of 2-ketoglutarate consuming enzymes like glutamate dehydrogenase or glutamate synthase (encoded by gdhA and gltB). These genes can be attenuated by replacing the natural promoter by a weaker promoter or by elements destabilizing the corresponding messenger RNA or the protein. If needed, complete attenuation of the gene can also be achieved by the deletion of the corresponding DNA sequence. The invention is also related to the microorganism, particularly a bacterium, used in this particular embodiment of the invention.

In a further embodiment of the invention, the microorganism, particularly a bacterium, is modified to present an attenuated level of 4-hydroxybutyraldehyde conversion to other compounds than 1,4-butanediol. This may be achieved by attenuating the level of 4-hydroxybutyraldehyde consuming enzymes like 4-hydroxybutyraldehyde dehydrogenase (encoded by aldA, aldB). These genes can be attenuated by replacing the natural promoter by a weaker promoter or by elements destabilizing the corresponding messenger RNA or the protein. If needed, complete attenuation of the gene can also be achieved by the deletion of the corresponding DNA sequence. The invention is also related to the microorganism, particularly a bacterium, used in this particular embodiment of the invention.

In a further embodiment of the invention, the microorganism, particularly a bacterium, is modified in order to produce 1,4-butanediol in anaerobic conditions. To achieve such capacity, in said microorganism, the PTS-sugar transport system is deleted in order to metabolize sugar via a permease/kinase transport system. In order to produce enough ATP for growth of the microorganism under anaerobic conditions, oxaloacetate must be produced from phosphoenolpyruvate via phosphoenolpyruvate carboxykinase activity encoded by the pckA gene in *E. coli*. This generates one mole of ATP per mole of oxaloacetate produced. In a similar manner, the conversion of 2-oxoglutarate into 4-oxoglutaryl-CoA must be achieved by 4-oxoglutaryl-CoA synthetase. The ADP-forming activity, such as encoded by the sucC and sucD genes in *E. coli*, consumes only one mole of ATP per mole of 4-oxoglutaryl-CoA produced. The described metabolic pathway to produce 1,4-butanediol from D-glucose is particularly adapted for anaerobic growth conditions. The global reaction balance of such pathway is: D-glucose+ADP+Pi→1,4-butanediol+formate+$CO_2$+ATP+$H_2O$. In a further embodiment of the invention, the microorganism, particularly a bacterium, is modified to present an attenuated level of acetyl-CoA conversion to other compounds than 1,4-butanediol; this result may be achieved by attenuating the level of acetyl-CoA consuming enzymes like acetate kinase and phosphate acetyltransferase (encoded by ackA and pta). Attenuation of these genes can be done by replacing the natural promoter by a lower strength promoter or by element destabilizing the corresponding messenger RNA or the protein. If needed, complete attenuation of the gene can also be achieved by a deletion of the corresponding DNA sequence. The invention is also related to the microorganism, particularly a bacterium, used in this particular embodiment of the invention.

DRAWINGS

FIG. 1. Biosynthesis pathway of ethylene glycol

FIG. 2. Biosynthesis pathway of 1,3-propanediol

FIG. 3. Biosynthesis pathway of 1,4-butanediol

FIG. 4. List of genes identified in the present application.

EXAMPLES

Example 1

Construction of Strains Expressing a 2-Keto Acid Decarboxylase Encoding Gene and a Hydroxy Aldehyde Reductase Encoding Gene: MG1655

(pME101-kivDll-yqhD-TT07)

1.1 Construction of the Plasmid pM-Ptrc01-kivDll-TT07 for the Overexpression of kivD of *Lactococcus lactis* Encoding Alpha-Keto-Isovalerate Decarboxylase:

A synthetic gene of the *Lactococcus lactis* kivD coding for the alpha-keto-isovalerate decarboxylase was prepared by Geneart (Germany). The codon usage and GC content of the gene was adapted to *Escherichia coli* according to the supplier matrix. Expression of the synthetic gene was driven by a constitutive Ptrc promoter. A transcriptional terminator was added downstream of the gene. The construct was cloned into supplier's pM vectors and verified by sequencing. If necessary, the synthetic gene was cloned into the pME101 vector (This plasmid is derived from plasmid pCL1920 (Lerner & Inouye, 1990, NAR 18, 15 p 4631)) before transforming an *E. coli* strain.

Ptrc01-kivDll-TT07:

```
restriction sites (BamHI, HindIII, EcoRV)
(SEQ ID NO 1):
ggatccatgcaagcttatgcgatatc Ptrc01 promoter (SEQ ID NO 2):
gagctgttgacaattaatcatccggctcgtataatgtgtggaataa ggaggtataac kivDll gene sequence optimized for E. coli
(CAG34226.) (SEQ ID NO 3):
atgtataccgtgggtgattatctgctggatcgtctgcatgaactgg gcattgaagaaattttcggcgttccgggtgattataatctgcagtt tctggatcagattattagccataaagatatgaaatgggtgggtaat gccaatgaactgaatgcaagctatatggcagatggttatgcccgta ccaaaaaagcagcagcatttctgaccacctttggtgttggtgaact gagcgcagttaatggtctggctggtagctatgcagaaaatctgccg gttgttgaaattgttggtagcccgaccagcaaagttcagaatgaag gcaaatttgtgcatcatacccctggccgatggtgattttaaacattt catgaaaatgcatgaaccggttaccgcagcacgtaccctgctgacc gcagaaaatgcaaccgttgaaattgatcgtgttctgagcgcactgc tgaaagaacgtaaaccggtgtatattaatctgccggtggatgttgc agcagcaaaagcagaaaaaccgagcctgccgctgaaaaaagaaat agcaccagcaataccagcgatcaggaaattctgaataaaattcagg aatccctgaaaaacgccaaaaaaccgattgtgattaccggtcatga aattattagctttggcctggaaaaaaccgttaccccagtttattagc aaaaccaaactgccgattaccaccctgaattttggtaaaagcagcg ttgatgaagcactgccgagctttctgggtatttataatggcaccct gagcgaaccgaatctgaaagaattgtgggaaagcgcagatttcatt ctgatgctgggtgttaaactgaccgatagctctaccggtgcattta cccatcatctgaatgaaaacaaaatgattagcctgaatattgatga aggcaaaattttttaatgaacgcattcagaattttgattttgaaagc ctgattagcagcctgctggatctgagcgaaatcgaatataaaggca aatatattgataaaaaacaggaagattttgttccgagcaatgcact gctgtctcaggatcgtctgtggcaggcagttgaaaatctgacccag agcaatgaaaccattgttgcagaacagggcaccagctttttttggtg caagcagcattttctgaaaagcaaaagccatttattggtcagcc gctgtgggtagcattggttatacctttccggcagcactgggtagc cagattgcagataaagaaagccgtcatctgctgtttattggtgatg gtagcctgcagctgaccgttcaggaactgggtctggccattcgcga aaaaattaatccgatttgctttattatcaataatgatggctatacc gtggaacgtgaaattcatggtccgaatcagagctataatgatattc cgatgtggaattatagcaaactgccggaatcttttggtgcaaccga agatcgtgttgtgagcaaaattgtgcgcaccgaaaatgaatttgtg agcgtgatgaaagaagcacaggcagatccgaatcgtatgtattgga
``` ttgaactgattctggccaaagaaggtgcaccgaaagttctgaaaaa aatgggcaaactgttcgccgaacagaataaaagctaa

```
terminator sequence T7Te (ref: Harrington
K. J., Laughlin R. B. and Liang S. Proc Natl
Acad Sci USA. 2001 Apr. 24; 98(9): 5019-24.)
(SEQ ID NO 4):
attacgtagaAGATCTtcctggctcaccttcgggtgggcctttctg restriction sites (SmaI, BamHI, EcoRI)
(SEQ ID NO 5):
ccccgggatgcggatccatgcgaattc
```

For the expression from a low copy vector the pME101 plasmid was constructed as follows. The pCL1920 plasmid was PCR amplified using the oligonucleotides PME101F and PME101R and the BstZ17I-XmnI fragment from the vector pTRC99A harboring the lad gene and the Ptrc promoter was inserted into the amplified vector. The resulting vector was restricted by NcoI and BamHI and the vector harboring the kivDll gene was restricted by AflIII and BamHI. The kivDll containing fragment was then cloned into the vector pME101: The resulting plasmid was named pME101-kivDll-TT07

PME101F (SEQ ID NO 6): ccgacagtaa gacgggtaag cctg

PME101R (SEQ ID NO 7): agcttagtaa agccctcgct ag 1.2 Construction of a Plasmid pME101-kivDll-yqhD-TT07 for the Overexpression of kivD of *Lactococcus lactis* Encoding Alpha-Ketoisovalerate Decarboxylase and yqhD of *Escherichia Coli* Encoding Methylglyoxal Reductase The pME101 vector and the vector harboring the kivDll genes were restricted by SnaBI and BglII and the yqhD containing fragment was cloned into the vector pME101, the resulting plasmid was named pME101-kivDll-yqhD-TT07.

The yqhD gene was PCR amplified from genomic DNA of the *E. coli* MG1655 strain with the oligonucleotides yqhD F and yqhD R:

(SEQ ID NO 8)
yqhD F    T*TACGTA*cccagcaaagggagcaagtaatgaacaac a region for addition of a SnaBI restriction site (italic bold upper case)

a region (lower case) homologous to the *E. coli* MG1655 yqhD region from 3153357 to 3153385

(SEQ ID NO 9)
yqhD R    a*agatct*cTTAGCGGGCGGCTTCGTATATAC a region (upper case) homologous to the *E. coli* MG1655 yqhD region from 3154540 to 3154518 a region for addition of a BglII restriction site (italic bold lower case).

The PCR amplified fragment was cut with the restriction enzymes SnaBI and BglII and cloned into the SnaBI-BglII sites of the vector pME101-kivDll-TT07 resulting in the vector pME101-kivDll-yqhD-TT07.

Example 2

Construction of Strains with Increased Ethylene Glycol Pathway Flux: MG1655 ΔsdaA ΔsdaB ΔpykF Ptrc18-gpmA Ptrc18-gpmB (pME101-kivDll-yqhD-TT07)

2.1 Construction of the MG1655 ΔsdaA ΔsdaB Strain

To delete the sdaA gene, the homologous recombination strategy described by Datsenko & Wanner (2000) was used. This strategy allowed the insertion of a chloramphenicol or a kanamycin resistance cassette, while deleting most of the genes concerned. For this purpose the following oligonucleotides were used:

ΔsdaAF (SEQ ID NO 10)
gtcaggagtattatcgtgattagtctat-tcgacatgtttaaggtggggattggtc-cctcatcttcccataccgtagggccTGTAG GCTGGAGCTGCTTCG with

- a region (lower case) homologous to the sequence (1894941-1895020) of the sdaA gene (reference sequence on the website http://genolist.pasteur.fr/Colibri/),
- a region (upper bold case) for the amplification of the kanamycin resistance cassette (reference sequence in Datsenko, K. A. & Wanner, B. L., 2000, PNAS, 97: 6640-6645), ΔdaAR (SEQ ID NO 11)
GGGCGAGTAAGAAGTATTAGTCACACTG-GACTTTGATTGCCAGACCACCGCGT GAG-GTTTCGCGGTATTTGGCGTTCATGTC-CCATATGAATATCCTCCTAAG with

- a region (upper case) homologous to the sequence (1896336-1896254) of the sdaA gene (reference sequence on the website http://genolist.pasteur.fr/Colibri/),
- a region (upper bold case) for the amplification of the kanamycin resistance cassette (reference sequence in Datsenko, K. A. & Wanner, B. L., 2000, PNAS, 97: 6640-6645).

The oligonucleotides ΔsdaAF and ΔsdaAR were used to amplify the kanamycin resistance cassette from the pKD4 plasmid. The PCR product obtained was then introduced by electroporation into the strain MG 1655 (pKD46). The kanamycin resistant transformants were selected and the insertion of the resistance cassette was verified by PCR analysis with the oligonucleotides sdaAF and sdaAR defined below. The strain retained was designated MG1655 ΔsdaA::Km. sdaAF (SEQ ID NO 12): cagcgttcgattcatctgcg (homologous to the sequence from 1894341 to 1894360). sdaAR (SEQ ID NO 13):
GACCAATCAGCGGAAGCAAG (homologous to the sequence from 1896679 to 1896660).

The kanamycin resistant transformants were then selected and the ΔsdaA::Km was verified by PCR analysis with the previously defined oligonucleotides sdaAF and sdaAR. The strain retained was designated MG1655 ΔsdaA::Km. Then the DsdaB::Cm was introduced into the strain MG1655 ΔsdaA::Km by transduction. The MG1655 ΔsdaB::Cm was first constructed using the same method as previously described with the following oligonucleotides:

ΔsdaBF (SEQ ID NO 14)
cggcattggcccttccagttctcatac-cgttggaccaatgaaagcgggtaaa-caatttaccgacgatctgattgcccgTGTAGG CTGGAGCTGCT-TCG with

- a region (lower case) homologous to the sequence (2927627-2927705) of the sdaB gene (reference sequence on the website http://genolist.pasteur.fr/Colibri/),
- a region (upper bold case) for the amplification of the chloramphenicol resistance cassette (reference sequence in Datsenko, K. A. & Wanner, B. L., 2000, PNAS, 97: 6640-6645), ΔsdaBR (SEQ ID NO 15)
CGCAGGCAACGATCTTCATTGCCAGGC-CGCCGCGAGAGGTTTCGCGGTACTTG GCGT-TCATATCTTTACCTGTTTCGTACCATAT-GAATATCCTCCTTAG with

- a region (upper case) homologous to the sequence (2928960-2928881) of the sdaB gene (reference sequence on the website http://genolist.pasteur.fr/Colibri/),
- a region (upper bold case) for the amplification of the chloramphenicol resistance cassette (reference sequence in Datsenko, K. A. & Wanner, B. L., 2000, PNAS, 97: 6640-6645). The oligonucleotides ΔsdaBF and ΔsdaBR were used to amplify the chloramphenicol resistance cassette from the plasmid pKD3. The PCR product obtained was then introduced by electroporation into the strain MG1655 (pKD46). The chloramphenicol resistant transformants were then selected and the insertion of the resistance cassette was verified by a PCR analysis with the oligonucleotides sdaBF and sdaBR defined below. The strain retained is designated MG1655 ΔsdaB::Cm. sdaBF (SEQ ID NO 16): Gcgtaagtacagcggtcac (homologous to the sequence from 2927450 to 2927468). sdaBR (SEQ ID NO 17): CGATGCCGGAACAGGCTACGGC (homologous to the sequence from 2929038 to 2929017). To transfer the ΔsdaB::Cm, the method of phage P1 transduction was used. The preparation of the phage lysate of the strain MG1655 ΔsdaB::Cm was used for the transduction into the strain MG1655 ΔsdaA::Km.

The chloramphenicol resistant transformants were then selected and the ΔsdaB::Cm was verified by a PCR analysis with the previously defined oligonucleotides sdaBF and sdaBR. The strain retained was designated MG1655 ΔsdaA:: Km ΔsdaB::Cm. The kanamycin and chloramphenicol resistance cassettes were then be eliminated. The plasmid pCP20 carrying FLP recombinase acting at the FRT sites of the kanamycin and the chloramphenicol resistance cassettes was then introduced into the recombinant sites by electroporation. After a series of cultures at 42° C., the loss of the kanamycin and chloramphenicol resistance cassettes was verified by a PCR analysis with the same oligonucleotides as used previously (sdaAF/sdaAR and sdaBF/sdaBR). The strain retained was designated MG1655 DsdaA ΔsdaB.

2.2 Construction of Strain MG1655 ΔsdaA ΔsdaB ΔpykF

To delete the pykF gene, the homologous recombination strategy described by Datsenko & Wanner (2000) was used.

This strategy allowed the insertion of a chloramphenicol or a kanamycin resistance cassette, while deleting most of the genes concerned. For this purpose the following oligonucleotides were used:

ΔpykFF (SEQ ID NO 18)

cccatccttctcaacttaaagactaa-gactgtcatgaaaaagaccaaaat-tgtttgcaccatcggaccgaaaaccgaaTGTAG GCTGGAGCTGCT-TCG with
- a region (lower case) homologous to the sequence (1753689-1753766) of the pykF region (reference sequence on the EcoGene website),
- a region (upper case) for the amplification of the kanamycin resistance cassette (reference sequence in Datsenko, K. A. & Wanner, B. L., 2000, PNAS, 97: 6640-6645), ΔpykFR (SEQ ID NO 19)

ggacgtgaacagatgcggtgttagtagt-gccgctcggtaccagtgcaccagaaac-cataactacaacgtcacctttgtgCATA TGAATATCCTCCTTAG with
- a region (upper case) homologous to the sequence (1755129-1755051) of the pykF region (reference sequence on the EcoGene website),
- a region (upper case) for the amplification of the kanamycin resistance cassette (reference sequence in Datsenko, K. A. & Wanner, B. L., 2000, PNAS, 97: 6640-6645).

The oligonucleotides ΔpykFF and ΔpykFR were used to amplify the kanamycin resistance cassette from the plasmid pKD4. The PCR product obtained was then introduced by electroporation into the strain MG 1655 (pKD46). The kanamycin resistant transformants were then selected and the insertion of the resistance cassette was verified by a PCR analysis with the oligonucleotides pykFF and pykFR defined below. The strain retained was designated MG1655 ΔpykF:: Km. pykFF (SEQ ID NO 20): gcgtaaccttttccctggaacg (homologous to the sequence from 1753371 to 1753392). pykFR (SEQ ID NO 21): gcgttgctggagcaacctgccagc (homologous to the sequence from 1755518 to 1755495).

To transfer the ΔpykF::Km, the method of phage P1 transduction was used. The preparation of the phage lysate of the strain MG1655 ΔpykF::Km was used for the transduction into the strain MG1655 ΔsdaA ΔsdaB.

The kanamycin resistant transformants were then selected and the ΔpykF::Km was verified by a PCR analysis with the previously defined oligonucleotides pykFF and pykFR. The strain retained was designated MG1655 ΔsdaA ΔsdaB ΔpykF::Km.

The kanamycin resistance cassette was then eliminated. The plasmid pCP20 carrying FLP recombinase acting at the FRT sites of the kanamycin resistance cassette was then introduced into the recombinant sites by electroporation. After a series of cultures at 42° C., the loss of the kanamycin resistance cassettes was verified by a PCR analysis with the same oligonucleotides as used previously (sdaAF/sdaAR, sdaBF/sdaBR and pykFF/pykFR). The strain retained was designated MG1655 ΔsdaA ΔsdaB ΔpykF.

2.3 Construction of Strain MG1655 ΔsdaA ΔsdaB ΔpykF Ptrc18-gpmA Ptrc18-gpmB

To increase the level of 3-phosphoglycerate, the mutants Ptrc18-gpmA and Ptrc18-gpmB are constructed. First, to reduce the expression of the phosphoglycerate mutase gpmA gene, the promoter is replaced by a modified constitutive trc promoter with weak activity.

The Ptrc18-gpmA is transferred into the MG1655 ΔsdaA ΔsdaB ΔpykF strain by transduction.

The strain MG1655 Ptrc18-gpmA::Km is first constructed using the same method as previously described with the following oligonucleotides:

Ptrc18-gpmAF (SEQ ID NO 22)

CCACTGACTTTCGCCATGACGAACCA-GAACCAGCTTAGTTACAGCCATAATAT ACCTCCT-TATTCCACACAgTATACGAGCCGGAT-GATTAATcGcCAACAGCTCTGT AGGCTGGAGCTGCTTCG with
- a region (upper case) homologous to the sequence (786771-786819) of the gpmA gene (reference sequence on the website http://genolist.pasteur.fr/Colibri/),
- a region (upper bold case) for the amplification of the kanamycin resistance cassette (reference sequence in Datsenko, K. A. & Wanner, B. L., 2000, PNAS, 97: 6640-6645),
- a region (upper italic case) for the trc promoter sequence where the −35 and −10 boxes are underlined.

Ptrc18-gpmAR (SEQ ID NO 23)

ggttatgcgtaagcattgctgttgct-tcgtcgcggcaatataatgagaattat-tatcattaaaagatgatttgaggagtaagtatCAT ATGAATATCCTCCT-TAG with
- a region (lower case) homologous to the sequence (786903-786819) of the region upstream of the gpmA gene (reference sequence on the website http://genolist.pasteur.fr/Colibri/),
- a region (upper bold case) for the amplification of the kanamycin resistance cassette (reference sequence in Datsenko, K. A. & Wanner, B. L., 2000, PNAS, 97: 6640-6645).

The oligonucleotides Ptrc18-gpmAF and Ptrc18-gpmAR are used to amplify the kanamycin resistance cassette from the plasmid pKD4. The obtained PCR product is then introduced by electroporation into the strain MG1655 (pKD46), in which the expressed Red recombinase enzyme permits the homologous recombination. The kanamycin resistant transformants are then selected, and the insertion of the resistance cassette is verified by a PCR analysis with the oligonucleotides gpmAF and gpmAR defined below. The strain retained is designated MG1655 Ptrc18-gpmA::Km. gpmAF (SEQ ID NO 24): CCTTCCTCTTTCAGCAGCTTACC (homologous to the sequence from 786673 to 786695). gpmAR (SEQ ID NO 25): cgacgatcagcgcaaagtgaaagg (homologous to the sequence from 787356 to 787333).

To transfer the modification Ptrc18-gpmA::Km, phage P1 transduction is used. The protocol followed is implemented in two steps, with first the preparation of the phage lysate of the strain MG1655 Ptrc18-gpmA::Km, and second the transduction into the strain MG1655 ΔsdaA ΔsdaB ΔpykF. The construction of the strain is described above.

1—Preparation of the P1 Phage Lysate

Inoculation with 100 µl of an overnight culture of the strain MG1655 Ptrc18-gpmA::Km of 10 ml of LB+Km 50 µg/ml+glucose 0.2%+CaCl2 5 mM. Incubation for 30 min at 37° C. with shaking. —Addition of 100 µl of phage lysate P1 prepared on the strain MG1655 (about $1.10^9$ phage/ml).

Shaking at 37° C. for 3 hours until all the cells were lysed. Addition of 200 µl chloroform and vortexing.

Centrifugation for 10 min at 4500 g to eliminate cell debris.
Transfer of supernatant to a sterile tube and addition of 200 µl chloroform.
Storage of lysate at 4° C.

2—Transduction

Centrifugation for 10 min at 1500 g of 5 ml of an overnight culture of the MG1655 ΔsdaA ΔsdaB ΔpykF strain in LB medium.
Suspension of the cell pellet in 2.5 ml of 10 mM MgSO$_4$, 5 mM CaCl2 Control tubes: 100 µl cells
100 µl phages P1 of strain MG1655 Ptrc18-gpmA::Km—Test tube: 100 µl of cells+100 µl of phages P1 of the strain MG1655 Ptrc18-gpmA::Km.
Incubation for 30 min at 30° C. without shaking. Addition of 100 µl of 1 M sodium citrate in each tube and vortex.
Addition of 1 ml of LB. —Incubation for 1 hour at 37° C. with shaking.
Spreading on dishes LB+Km 50 mg/ml after centrifugation of tubes for 3 min at 7000 rpm.
Incubation at 37° C. overnight.

3—Verification of the Strain

The kanamycin resistant transformants are then selected and the modification of the promoter Ptrc18-gpmA::Km is verified by a PCR analysis with the oligonucleotides gpmAF and gpmAR previously described. The strain retained is designated MG1655 ΔsdaA ΔsdaB ΔpykF Ptrc18-gpmA::Km. Then the Ptrc18-gpmB is transferred into the MG1655 ΔsdaA ΔsdaB ΔpykF Ptrc18-gpmA::Km strain by transduction. The MG1655 Ptrc18-gpmB::Cm is first constructed using the same method as previously described with the following oligonucleotides:

Ptrc18-gpmBR (SEQ ID NO 26)
CGGCGTTCC ACTGCGTTTCACCGTGGCGGAC-TAGGTATACCTGTAACATAATATACCTCCTTA TTCCA-CACAgTATACGAGCCGGATGAT-TAATcGcCAACAGCTCTGTAGGCTGGA GCTGCTTCG
with
a region (upper case) homologous to the sequence (4631414-4631366) of the gpmB gene (reference sequence on the website http://genolist.pasteur.fr/Colibri/),
a region (upper bold case) for the amplification of the chloramphenicol resistance cassette (reference sequence in Datsenko, K. A. & Wanner, B. L., 2000, PNAS, 97:6640-6645),
a region (upper italic case) for the trc promoter sequence where the −35 and −10 boxes are underlined.
Ptrc18-gpmBF (SEQ ID NO 27)
agggattggtggtcgcacagacaacttg-gtgcataatcagcattactcagaaaattaacgttacagcagtatacggaaaaaaagc CATATGAATATCCTCCTTAG with
a region (lower case) homologous to the sequence (4631280-4631365) of the region upstream of the gpmB gene (reference sequence on the website http://genolist.pasteur.fr/Colibri/),
a region (upper bold case) for the amplification of the chloramphenicol resistance cassette (reference sequence in Datsenko, K. A. & Wanner, B. L., 2000, PNAS, 97: 6640-6645).

The oligonucleotides Ptrc18-gpmBF and Ptrc18-gpmBR are used to amplify the chloramphenicol resistance cassette from the plasmid pKD3. The PCR product obtained is then introduced by electroporation into the strain MG1655 (pKD46), in which the Red recombinase enzyme expressed, permits the homologous recombination. The chloramphenicol resistant transformants are then selected and the insertion of the resistance cassette is verified by a PCR analysis with the oligonucleotides gpmBF and gpmBR defined below. The strain retained is designated MG1655 Ptrc18-gpmB::Cm gpmBF (SEQ ID NO 28): ccttacgaccaatctcatcaataccgg (homologous to the sequence from 4630906 to 4630932).
gpmBR (SEQ ID NO 29): GCAATACCATGACTCAC-CAGC (homologous to the sequence from 4631823 to 4631803).

To transfer the modification Ptrc18-gpmB::Cm, phage P1 transduction is used. Phage lysate of the strain MG1655 Ptrc18-gpmB::Cm is used for the transduction into the strain MG1655 ΔsdaA ΔsdaB ΔpykF Ptrc18-gpmA::Km. The chloramphenicol resistant transformants are then selected and the Ptrc18-gpmB::Cm is verified by a PCR analysis with the previously defined oligonucleotides gpmBF and gpmBR. The strain retained is designated MG1655 ΔsdaA ΔsdaB ΔpykF Ptrc18-gpmA::Km Ptrc18-gpmB::Cm. The kanamycin and chloramphenicol resistance cassettes can then be eliminated. The plasmid pCP20 carrying FLP recombinase acting at the FRT sites of the kanamycin and the chloramphenicol resistance cassettes is then introduced into the recombinant sites by electroporation. After a series of cultures at 42° C., the loss of the kanamycin and chloramphenicol resistance cassettes is verified by a PCR analysis with the same oligonucleotides as used previously (gpmAF/gpmAR and gpmBF/gpmBR). The strain retained is designated MG1655 ΔsdaA ΔsdaB ΔpykF Ptrc18-gpmA Ptrc18-gpmB.

2.4 Construction of the MG1655 ΔsdaA ΔsdaB ΔpykF Ptrc18-gpmA Ptrc18-gpmB (pME101-kivDll-yqhD-TT07) Strain The pME101-kivDll-yqhD-TT07 plasmid is then introduced into the strain MG1655 ΔsdaA ΔsdaB ΔpykF Ptrc18-gpmA Ptrc18-gpmB.

Example 3

Construction of Strains with Increased 1,3-Propanediol Pathway Flux: MG1655 ΔmetA ΔpykF ΔthrLABC::TT07-Ptrc-thrA*1 (pME101-kivDll-yqhD-TT07) (pMA-Aaoro)

3.1 Construction of Strain MG1655 ΔmetA

To delete the metA gene, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used:

ΔmetAF (SEQ ID NO 30):
ttcgtgtgccggacgagctacccgccgt-caatttatgcgtgaagaaaacgtattgtgatgacaacttacgtgcgtaTGTAG GCTGGAGCTGCTTCG
with
a region (lower case) homologous to the sequence (4212310-4212389) of the metA region (reference sequence on the EcoGene website),
a region (upper case) for the amplification of the kanamycin resistance cassette (reference sequence in Datsenko, K. A. & Wanner, B. L., 2000, PNAS, 97: 6640-6645), ΔmetAR (SEQ ID NO 31):
atccagcgttggattcatgtgccgta-gatcgtatggcgtgatctggtagacg-taatagttgagccagttggtaaacagtaCATAT GAATATCCTCCT-TAG
with
a region (upper case) homologous to the sequence (4213229-4213150) of the metA region sequence on the EcoGene website), a region (upper case) for the amplification of the kanamycin resistance cassette (reference sequence in Datsenko, K. A. & Wanner, B. L., 2000, PNAS, 97: 6640-6645).

The oligonucleotides ΔmetAF and ΔmetAR were used to amplify the kanamycin resistance cassette from the plasmid pKD4. The PCR product obtained was then introduced by electroporation into the strain MG 1655 (pKD46). The kanamycin resistant transformants were then selected and the insertion of the resistance cassette was verified by a PCR analysis with the oligonucleotides metAF and metAR defined below. The strain retained was designated MG1655 ΔmetA::Km. metAF (SEQ ID NO 32): tcaccttcaacatgcaggctcgacattggc (homologous to the sequence from 4212203 to 4212232). metAR (SEQ ID NO 33): ataaaaaaggcacccgaaggtgcctgaggt (homologous to the sequence from 4213301 to 4213272).

The kanamycin resistance cassette was then eliminated. The plasmid pCP20 carrying FLP recombinase acting at the FRT sites of the kanamycin resistance cassette was then introduced into the recombinant sites by electroporation. After a series of cultures at 42° C., the loss of the kanamycin resistance cassette was verified by a PCR analysis with the same oligonucleotides as used previously (metAF/metAR). The strain retained was designated MG1655 ΔmetA.

3.2 Construction of Strain MG1655 ΔmetA ΔpykF

To transfer the ΔpykF::Km, phage P1 transduction was used. The preparation of the phage lysate of the strain MG1655 ΔpykF::Km (described above) was used for the transduction into the strain MG1655 ΔmetA.

Kanamycin resistant transformants are then selected and the ΔpykF::Km was verified by a PCR analysis with the previously defined oligonucleotides pykFF and pykFR. The strain retained was designated MG1655 ΔmetA DpykF::Km.

3.3 Construction of Strain MG1655 DmetA DpykF DthrLABC::TT07-Ptrc-thrA*1

To increase the expression of the feedback resistant allele of the aspartokinase/homoserine dehydrogenase, thrA*1, the following plasmids were constructed: pSB1 to obtain the thrA*1 and pSB2 to replace the thrLABC operon by the Ptrc-thrA*1 allele.

The plasmid pSB1 is derived from plasmid pCL1920 (Lerner & Inouye, 1990, NAR 18, 15 p 4631) and harbors the aspartokinase/homoserine thrA*allele with reduced feedback resistance to threonine (Lee et al. 2003 J. Bacteriol. 185, 18 pp. 5442-5451) expressed from the promoter Ptrc. For the construction of pSB1, thrA was PCR amplified from genomic DNA using the following oligonucleotides:

BspHIthrA (SEQ ID NO 34):
TTATCATGAgagtgttgaagttcggcggtacatcagtggc
with
   a region (lower case) homologous to the sequence (341-371) of the thrA gene (reference sequence on the website http://www.ecogene.org/),
   a region (upper case) for BspHI restriction site and extra-bases,
SmaIthrA (SEQ ID NO 35):
TTACCCGGGccgccgccccgagcacatcaaacccgacgc
with
   a region (lower case) homologous to the sequence (2871-2841) of the thrA gene (reference sequence on the EcoGene website),
   a region (upper case) for SmaI restriction site and extra-bases.

The PCR amplified fragment was cut with the restriction enzymes BspHI and SmaI and cloned into the NcoI/SmaI sites of the vector pTRC99A (Stratagene). For the expression from a low copy vector the pME101 plasmid was constructed as follows. The pCL1920 plasmid was PCR amplified using the oligonucleotides PME101F and PME101R and the BstZ17I-XmnI fragment from the pTRC99A vector harboring the lad gene and the Ptrc promoter was inserted into the amplified vector. The resulting vector and the vector harboring the thrA gene were restricted by ApaI and SmaI and the thrA containing fragment was cloned into the vector pME101. To relieve ThrA from feedback inhibition the mutation thrAS345F was introduced by site-directed mutagenesis (Stratagene) using the oligonucleotides ThrA SF for and ThrA SF rev, resulting in the vector pSB1.

```
PME101F
                                                (SEQ ID NO 36)
ccgacagtaagacgggtaagcctg PME101R
                                                (SEQ ID NO 37)
agcttagtaaagccctcgctag ThrA SF for
                                                (SEQ ID NO 38)
CGTATTTCCGTGGTGCTGATTACGCAATTCTCTTCCGAGTACTCAATC

AGTTTCTGC

ThrA SF rev
                                                (SEQ ID NO 39)
GCAGAAACTGATTGAGTACTCGGAAGAGAATTGCGTAATCAGCACCAC

GGAAATACG
```

To delete the thrLABC operon and replace it by Ptrc-thrA*1 allele, the homologous recombination strategy described by Datsenko & Wanner (2000) was used. This strategy allows the insertion of a chloramphenicol or a kanamycin resistance cassette but also of additional DNA, while deleting most of the genes concerned. For this purpose, the following plasmid was constructed, pSB2.

The plasmid pSB2 is derived from plasmid pUC18 (Norrander et al., Gene 26 (1983), 101-106) and harbours the chloramphenicol resistance cassette associated to Ptrc-thrA*1 allele, both cloned between the upstream region of thrL and the downstream region of thrC.

For the construction of pSB2, the upstream region of thrL and the downstream region of thrC were PCR amplified from genomic DNA using the following oligonucleotides:
HpaIupthrLF (SEQ ID NO 40)
CGTAGTTAACGAATTCccaactagttg-catcatacaactaataaacgtgg
with
   a region (lower case) homologous to the sequence (4638698-4638731) of the thrL region (reference sequence on the EcoGene website),
   a region (upper case) for HpaI and EcoRI restriction site and extra-bases. BstZ17IupthrLR (SEQ ID NO 41) CCCGGGGGAGGCGCCCGCGGATCCGG-TATACCAGAAAGGCCCACCCGAAG GTGAGCCAG-GAaggtaaccagttcagaagagetatcag
with
   a region (lower case) homologous to the sequence (87-60) of the thrL region (reference sequence on the EcoGene website),
   a region (upper bold case) for T7te transcriptional terminator sequence (Harrington K. J., Laughlin R. B. and Liang S. Proc Natl Acad Sci USA. 2001 Apr. 24; 98(9): 5019-24),
   a region (upper case) for the multiple cloning site composed of BstZ17I, BamHI, SfoI and SmaI restriction sites.

BamHIdownthrCF (SEQ ID NO 42)
TCCTGGCTCACCTTCGGGTGGGC-
CTTTCTGGTATACCGGGATCCGCGGGCG CCTC-
CCCCGGGaatctattcattatctcaatcaggccggg
with
- a region (lower case) homologous to the sequence (5021-5049) of the thrC region (reference sequence on the EcoGene website),
- a region (upper bold case) for T7te transcriptional terminator sequence (Harrington K. J., Laughlin R. B. and Liang S. Proc Natl Acad Sci USA. 2001 Apr. 24; 98(9): 5019-24),
- a region (upper case) for the multiple cloning site composed of BstZ17I, BamHI, SfoI and
- SmaI restriction sites.

HpaIdownthrCR (SEQ ID NO 43)
CGTAGTTAACGAATTCgagaatgcccgagggaaagatctg
with
- a region (lower case) homologous to the sequence (6054-6031) of the thrC region (reference sequence on the EcoGene website),
- a region (upper case) for HpaI and EcoRI restriction site and extra-bases. First, the "upthrL" and "downthrC" fragments were PCR amplified from MG1655 genomic DNA using HpaIupthrLF/BstZ17IupthrLR and BamHIdownthrCF/HpaIdownthrCR oligonucleotides, respectively. Secondly, the"upthrL-downthrC" fragment was amplified from "upthrL" and "downthrC" PCR fragments (that possess an overlapping region composed of a T7Te transcriptional terminator and the multiple cloning site composed of BstZ17I, BamHI, SfoI and SmaI restriction sites) using HpaIupthrLF/HpaIdownthrCR oligonucleotides. The "upthrL-downthrC" PCR fragment was cut with the restriction enzyme HpaI and cloned into the EcoRI/SfoI sites of the pUC18 vector, giving the pUC18-DthrLABC::TT07-SMC plasmid.

Then, the chloramphenicol resistance cassette was PCR amplified from pKD3 vector using the following oligonucleotides:

BstZ17ICmF (SEQ ID NO 44)
GGGGTATACtgtaggctggagctgcttcg
with
- a region (lower case) for the amplification of the chloramphenicol resistance cassette (reference sequence in Datsenko, K. A. & Wanner, B. L., 2000, PNAS, 97: 6640-6645),
- a region (upper case) for BstZ17I restriction site and extra-bases.

BamHICmR (SEQ ID NO 45)
CGCGGATCCcatatgaatatcctccttag
with
- a region (lower case) for the amplification of the chloramphenicol resistance cassette (reference sequence in Datsenko, K. A. & Wanner, B. L., 2000, PNAS, 97: 6640-6645),
- a region (upper case) for BamHI restriction site and extra-bases.

The PCR fragment was cut with the restriction enzymes BstZ17I and BamHI and cloned into the BstZ17I/BamHI sites of the pUC18-ΔthrLABC::TT07-SMC plasmid, giving the pUC18-ΔthrLABC::TT07-SMC::Cm plasmid.

Finally, the Ptrc-thrA*1 allele was cut from the pSB1 plasmid with the restriction enzymes SfoI and SmaI and cloned into the SfoI/SmaI sites of the pUC18-ΔthrLABC::TT07-SMC::Cm plasmid, giving the pUC18-ΔthrLABC::TT07-Ptrc-thrA*1::Cm plasmid or pSB2.

The ΔthrLABC::TT07-Ptrc-thrA*1::Cm fragment was obtained by cutting the pSB2 plasmid with EcoRI restriction enzyme and was then introduced by electroporation into the strain MG1655 (pKD46), in which the expressed Red recombinase enzyme permits the homologous recombination. The chloramphenicol resistant transformants are then selected, and the insertion of the resistance cassette is verified by a PCR analysis with the oligonucleotides thrA*1F and thrA*1R defined below. The strain retained is designated MG1655 ΔthrLABC::TT07-Ptrc-thrA*1::Cm. thrA*1F (SEQ ID NO 46): cgtgttgcgtgttaccaactcg (homologous to the sequence (4638276-4638297) of the thrL region (reference sequence on the EcoGene website)). thrA*1R (SEQ ID NO 47) cggaaactgacgcctccgcag (homologous to the sequence (6345-6325) of the thrC region (reference sequence on the EcoGene website)).

Recombinant plasmids were verified by DNA sequencing.

To transfer the ΔthrLABC::TT07-Ptrc-thrA*1::Cm, phage P1 transduction is used. The preparation of the phage lysate of the strain MG1655 ΔthrLABC::TT07-Ptrc-thrA*1::Cm is used for the transduction into the strain MG1655 ΔmetA DpykF::Km.

The kanamycin and chloramphenicol resistant transformants are then selected and the ΔthrLABC::TT07-Ptrc-thrA*1::Cm is verified by a PCR analysis with the previously defined oligonucleotides thrA*1F and thrA*1R. The strain retained is designated MG1655 ΔmetA ΔpykF::Km ΔthrLABC::TT07-Ptrc-thrA*1::Cm.

The kanamycin and chloramphenicol resistance cassettes can then be eliminated. The plasmid pCP20 carrying FLP recombinase acting at the FRT sites of the kanamycin and chloramphenicol resistance cassettes is then introduced into the recombinant sites by electroporation. After a series of cultures at 42° C., the loss of the kanamycin and chloramphenicol resistance cassettes is verified by a PCR analysis with the same oligonucleotides as used previously (metAF/metAR, pykF/pykFR and thrA*1F/thrA*1R). The strain retained is designated MG1655 ΔmetA ΔpykF ΔthrLABC::TT07-Ptrc-thrA*1.

3.4 Construction of Plasmid pMA-aaoro

A synthetic gene of the *Rhodococcus opacus* aao gene coding for amino acid oxidase was prepared by the Geneart (Germany). The codon usage and GC content of the genes was adapted to *Escherichia coli* according to the supplier matrix. Expression of the synthetic gene was driven by a constitutive Ptrc promoter. The construct was cloned into supplier's pMA vector and verified by sequencing.

Ptrc01-aaoro:

```
restriction sites (KpnI, EcoRI, SmaI)
(SEQ ID NO 48):
ggtaccgaattccccggg

Ptrc01 promoter and RBS (SEQ ID NO 49):
gagctgttgacaattaatcatccggctcgtataatgtgtggaaggatc
ccccgggtaaggaggttataa aaoro gene sequence optimized for E. coli
(AY053450.) (SEQ ID NO 50):
atggcatttacccgtcgcagctttatgaaaggtctgggtgcaaccggt
ggtgcaggtctggcatatggtgcaatgagcaccctgggtctggcaccg
tctacagcagcaccggcacgtacctttcagccgctggcagccggtgat
ctgattggtaaagtgaaaggtagccatagcgttgttgttctgggtggt
ggtccggcaggtctgtgtagcgcatttgaactgcagaaagccggttat
aaagttaccgttctggaagcacgtacccgtccgggtggtcgtgtttgg
accgcacgtggtggtagcgaagaaaccgatctgagcggtgaaacccag
aaatgtacctttagcgaaggccatttttataatgttggtgccacccgt
attccgcagagccatattaccctggattattgtcgcgaactgggtgtt
gaaattcagggtttcggcaatcaaaatgccaataccttttgtgaattat
```

-continued

```
cagagcgataccagcctgagcggtcagagcgttacctatcgtgcagca
aaagcagataccctttggctatatgagcgaactgctgaaaaaagcaacc
gatcagggtgcactggatcaggttctgagccgtgaagataaagatgca
ctgagcgaatttctgagcgattttggtgatctgtctgatgatggtcgt
tatctgggtagcagccgtcgtggttatgatagcgaaccgggtgccggt
ctgaattttggcaccgaaaaaaaaccgtttgccatgcaggaagttatt
cgtagcggtattggtcgcaattttagctttgattttggctatgatcag
gccatgatgatgtttacaccggttggtggtatggatcgtatttattat
gcctttcaggatcgtattggcactgataacatcgtgttcggtgccgaa
gttaccagcatgaaaaatgttagcgaaggtgtgaccgttgaatatacc
gcaggcggtagcaaaaaaagcattaccgcagattatgccatttgtacc
attcctccgcatctggttggtcgtctgcagaataatctgcctggtgat
gttctgaccgcactgaaagcagcaaaaccgagcagcagcggtaaactg
ggtattgaatatagccgtcgttggtgggaaaccgaagatcgcatttat
ggtggtgcaagcaataccgataaagatattagccagattatgtttccg
tatgatcattataatagcgatcgtggtgttgttgttgcatattatagc
tctggtaaacgccaggaagcatttgaaagcctgacccatcgtcagcgt
ctggcaaaagcaattgcagaaggcagcgaaattcacggcgaaaaatat
acccgtgatattagcagcagctttagcggtagctggcgtcgtaccaaa
tatagcgaaagcgcatgggcaaattgggcaggtagcggtggttctcat
ggtggtgcagccactccggaatatgaaaaactgctggaaccggtggat
aaaattatttgccggtgatcatctgagcaatgcaatcgcatggcag
catggtgcactgaccagcgcacgtgatgttgttacccatattcatgaa
cgtgttgcacaggaagcctaa restriction sites (BglII, EcoRV, PacI, SacI,
XbaI, HindIII) (SEQ ID NO 51):
gatctgatatcttaattaagagctctctagaaagctt
```

3.5 Construction of Strain MG1655 ΔmetA ΔpykF Δthr-LABC::TT07-Ptrc-thrA*1 (pME101-kivDll-yqhD-TT07) (pMA-aaoro)

The pME101-kivDll-yqhD-TT07 and the pMA-aaoro plasmids are then introduced into the strain MG1655 ΔmetA ΔpykF ΔthrLABC::TT07-Ptrc-thrA*1.

Example 4

Construction of Strains with Increased 1,4-Butanediol Pathway Flux: MG1655 ΔsucCD ΔaceBAK ΔarcA ΔgdhA (pUC19-Ptrc01/OP01/RBS01-adhE2ca-prpE-TT02) (pME101-kivDll-yqhD-TT07)

4.1 Construction of Strain MG1655 ΔaceBAK ΔsucCD

To delete the aceBAK genes, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used:

ΔaceBAKF (SEQ ID NO 52):
ctggattcacaaggccgtatggcgag-caggagaagcaaattcttactgc-cgaagcggtagaatttctgactgagaggtTGTA GGCTGGAGCT-GCTTCG
with
a region (lower case) homologous to the sequence (4213531-4213610) of the aceB region (reference sequence on the EcoGene website),
a region (upper bold case) for the amplification of the kanamycin resistance cassette (reference sequence in Datsenko, K. A. & Wanner, B. L., 2000, PNAS, 97: 6640-6645), ΔaceBAKR (SEQ ID NO 53):
aacatcttccacatgcccttcacgtat-gcggttttgtagtgcgcgccagtaat-cagcgcggaacaggtcggcgtgcatcCATAT GAATATCCTCCT-TAG
with
a region (upper case) homologous to the sequence (4218298-4218220) of the aceK region (reference sequence on the EcoGene website),
a region (upper bold case) for the amplification of the kanamycin resistance cassette (reference sequence in Datsenko, K. A. & Wanner, B. L., 2000, PNAS, 97: 6640-6645).

The oligonucleotides ΔaceBAKF and ΔaceBAKR are used to amplify the kanamycin resistance cassette from the plasmid pKD4. The PCR product obtained is then introduced by electroporation into the strain MG 1655 (pKD46). The kanamycin resistant transformants are then selected and the insertion of the resistance cassette is verified by a PCR analysis with the oligonucleotides aceBAKF and aceBAKR defined below. The strain retained is designated MG1655 ΔmetA::Km. aceBAKF (SEQ ID NO 54): cgttaagcgattcagcaccttacc (homologous to the sequence from 4213251 to 4213274). aceBAKR (SEQ ID NO 55): aacgcattacccactctgtttaatacg (homologous to the sequence from 4218728 to 4218702).

To delete the sucCD genes, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used:

ΔsucCDF (SEQ ID NO 56):
tttttgcccgctatggcttaccagcac-cggtgggttatgcctgtactactc-cgcgcgaagcagaagaagccgcttcaaaaCATA TGAATATCCTC-CTTAG
with
a region (lower case) homologous to the sequence (762268-762347) of the sucC region (reference sequence on the EcoGene website),
a region (upper bold case) for the amplification of the chloramphenicol resistance cassette (reference sequence in Datsenko, K. A. & Wanner, B. L., 2000, PNAS, 97: 6640-6645), ΔsucCDR (SEQ ID NO 57):
atatccgccaggctgcgaacg-gttttcacgcctgcggcttccagag-cagcgaatttctcatccgcagtcccttaccggcTGTA GGCTGGAGCT-GCTTCG
with
a region (upper case) homologous to the sequence (764241-764168) of the sucD region (reference sequence on the EcoGene website),
a region (upper bold case) for the amplification of the chloramphenicol resistance cassette (reference sequence in Datsenko, K. A. & Wanner, B. L., 2000, PNAS, 97: 6640-6645).

The oligonucleotides DsucCDF and DsucCDR are used to amplify the chloramphenicol resistance cassette from the plasmid pKD3. The PCR product obtained is then introduced by electroporation into the strain MG 1655 (pKD46). The chloramphenicol resistant transformants are then selected and the insertion of the resistance cassette is verified by a PCR analysis with the oligonucleotides sucCDF and sucCDR defined below. The strain retained is designated MG1655 ΔsucCD::Cm. sucCDF (SEQ ID NO 58): tcgcgaatccgtgggct-tcctggtaacg (homologous to the sequence from 761887 to 761914). sucCDR (SEQ ID NO 59): cctctgatgccaaccgaa-gagatgagccg (homologous to the sequence from 764555 to 764527).

To transfer the ΔaceBAK::Km, the method of phage P1 transduction is used. The preparation of the phage lysate of the strain MG1655 DaceBAK::Km is used for the transduction into the strain MG1655 ΔsucCD::Cm.

The kanamycin and chloramphenicol resistant transformants are then selected and the ΔaceBAK::Km is verified by a PCR analysis with the previously defined oligonucleotides aceBAKF and aceBAKR. The strain retained is designated MG1655 ΔsucCD::Cm ΔaceBAK::Km.

The kanamycin and chloramphenicol resistance cassettes can then be eliminated. The plasmid pCP20 carrying FLP recombinase acting at the FRT sites of the kanamycin and chloramphenicol resistance cassettes is then introduced into the recombinant sites by electroporation. After a series of cultures at 42° C., the loss of the kanamycin and chloramphenicol resistance cassettes is verified by a PCR analysis with the same oligonucleotides as used previously (aceBAKF/aceBAKR, and sucCDF/sucCDR). The strain retained is designated MG1655 ΔsucCD ΔaceBAK.

4.2 Construction of Strain MG1655 ΔsucCD ΔaceBAK ΔarcA ΔgdhA

To delete the arcA gene, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used:

ΔarcAF (SEQ ID NO 60): cccgcacattatatcgttgaagacgagt-tggtaacacgcaacacgttgaaaag-tattttcgaageggaaggctatgTGTAGG CTGGAGCTGCTTCG
with
  a region (lower case) homologous to the sequence (4638322-4638245) of the arcA region (reference sequence on the EcoGene website),
  a region (upper bold case) for the amplification of the kanamycin resistance cassette (reference sequence in Datsenko, K. A. & Wanner, B. L., 2000, PNAS, 97: 6640-6645), ΔarcAR (SEQ ID NO 61):
ccagatcaccgcagaagcgataacct-tcaccgtgaatggtggcgatgatttccg-gcgtatccggcgtagattcgaaatgCATA TGAATATCCTCCTTAG
with
  a region (upper case) homologous to the sequence (4637621-4637699) of the arcA region (reference sequence on the EcoGene website),
  a region (upper bold case) for the amplification of the kanamycin resistance cassette (reference sequence in Datsenko, K. A. & Wanner, B. L., 2000, PNAS, 97: 6640-6645).

The oligonucleotides DarcAF and DarcAR are used to amplify the kanamycin resistance cassette from the plasmid pKD4. The PCR product obtained is then introduced by electroporation into the strain MG 1655 (pKD46). The kanamycin resistant transformants are then selected and the insertion of the resistance cassette is verified by a PCR analysis with the oligonucleotides arcAF and arcAR defined below. The strain retained is designated MG1655 ΔarcA::Km. arcAF (SEQ ID NO 62): cgacaattggattcaccacg (homologous to the sequence from 4638746 to 4638727). arcAR (SEQ ID NO 63): gcggtattgaaaggttggtgc (homologous to the sequence from 4637308 to 4637328).

To transfer the ΔarcA::Km, phage P1 transduction is used. Phage lysate of the strain MG1655 DarcA::Km is used for the transduction into the strain MG1655 ΔsucCD ΔaceBAK.

The kanamycin resistant transformants are then selected and the ΔarcA::Km is verified by a PCR analysis with the previously defined oligonucleotides arcAF and arcAR. The strain retained is designated MG1655 ΔsucCD ΔaceBAK ΔarcA::Km.

To delete the gdhA gene, the homologous recombination strategy described by Datsenko & Wanner (2000) was used.

The oligonucleotides ΔgdhAF and ΔgdhAR are used to amplify the chloramphenicol resistance cassette from the plasmid pKD3.

ΔgdhAF (SEQ ID NO 64): taaacaacataagcacaatcgtat-taatatataagggttttatatctatgTGTAGGCTGGAGCTGCTTCG
with
  a region (lower case) homologous to the sequence (1840348 to 1840397) upstream of the gene gdhA (http://ecogene.org/blast.php)
  a region (upper bold case) for the amplification of the chloramphenicol resistance cassette (reference sequence in Datsenko, K. A. & Wanner, B. L., 2000, PNAS, 97: 6640-6645), ΔgdhAR (SEQ ID NO 65): taagcgtagcgccatcaggcattta-caacttaaatcacaccctgcgccagCATATGAATATCCTCCTTAG
with:
  a region (lower case) homologous to the sequence (1841767 to 1841718) to the end and the downstream region of the gdhA gene (http://ecogene.org/blast.php)
  a region (upper bold case) for the amplification of the chloramphenicol resistance cassette (reference sequence in Datsenko, K. A. & Wanner, B. L., 2000, PNAS, 97: 6640-6645), The PCR product obtained is then introduced by electroporation into the MG1655 (pKD46) strain. The chloramphenicol resistant transformants are then selected and the insertion of the resistance cassette is verified by a PCR analysis with oligonucleotides Ptrc-gdhAverF and gdhA R.

```
Ptrc-gdhAverF(SEQ ID NO 66):
CCTTAACGTTATTGTCTCTGC
``` a region homologous to the sequence (1840168-1840188) of the region upstream of the gdhA gene (http://ecogene.org/blast.php)

```
gdhA R(SEQ ID NO 67):
GGAGGAAGCCCCAGAGCAGG
``` a region homologous to the sequence (1842274-1842293) of the region downstream of the gdhA gene (http://ecogene.org/blast.php).

The strain obtained was named MG1655 ΔgdhA::Cm.

To transfer the ΔgdhA::Cm, phage P1 transduction is used. Phage lysate of the strain MG1655 ΔgdhA::Cm is used for the transduction into the strain MG1655 ΔsucCD ΔaceBAK ΔarcA::Km.

The kanamycin and chloramphenicol resistant transformants are then selected and the ΔgdhA::Cm is verified by a PCR analysis with the previously defined oligonucleotides Ptrc-gdhAverF and gdhA R. The strain retained is designated MG1655 ΔsucCD ΔaceBAK ΔarcA::Km ΔgdhA:: Cm.

The kanamycin and chloramphenicol resistance cassettes can then be eliminated. The plasmid pCP20 carrying FLP recombinase acting at the FRT sites of the kanamycin and chloramphenicol resistance cassettes is then introduced into the recombinant sites by electroporation. After a series of cultures at 42° C., the loss of the kanamycin and chloramphenicol resistance cassettes is verified by a PCR analysis with the same oligonucleotides as used previously (aceBAKF/aceBAKR, sucCDF/sucCDR, arcAF/arcAR, and gdhAverF/gdhA R). The strain retained is designated MG1655 ΔsucCD ΔaceBAK ΔarcA ΔgdhA.

4.3 Construction of a Plasmid for Overexpression of the Bifunctional Acetaldehyde-CoA/alcohol dehydrogenase adhE2 of *Clostridium acetobutylicum* and the propionyl-CoA synthetase prpE gene of *Escherichia coli*: pUC19-Ptrc01/OP01/RBS01-adhE2ca-prpE-TT02

The adhE2 gene from *Clostridium acetobutylicum* coding for the bifunctional acetaldehyde-CoA/alcohol dehydrogenase was cloned in the plasmid pUC19. The prpE gene coding for the propionyl-CoA synthetase was cloned upstream adhE2.

The adhE2 gene was PCR amplified from the megaplasmid pSol1 of the *Clostridium acetobutylicum* strain ATCC824 (position 33722 to 36298) with the oligonucleotides adhE2Ca F and adhE2Ca R.

adhE2Ca F (SEQ ID NO 68):
ggtaccggatccgggccc
gagagttgacaattaatcatccggctcgtataatgtgtggaattgtgagc ggataa-
caattTACG TAtaaggaggtatatt
ATGAAAGTTACAAATCAAAAAGAAC with region (bold lower case) for the addition of KpnI, BamHI, ApaI restriction site
region (underlined lower case) for the addition of the promoter Ptrc01
region (italic lower case) for the addition of an operator sequence OP01
region (bold upper case) for the addition of SnaBI restriction site
region (lower case) for the addition RBS01 sequence
region (underlined upper case) homologous the *C. acetobutylicum* adhE2 region from 33722 to 33752 adhE2Ca R (SEQ ID NO 69):
GAGCTCAAGCTT
aacagataaaacgaaaggcccagtctttcgactgagcctttcgttttatttgatgc
ctagggcta gctctagattaa
TTAAAATGATTTTATATAGATATCCTTAAGTTCAC,
with region (upper case) for the addition of the HindIII, SacI restriction site.
region (underlined bold lower case) for the addition of the terminator TT02
region (italic case) for the addition of the PacI, XbaI, NheI, AvrII restriction site
region (underlined upper case) homologous the *C. acetobutylicum* adhE2 region from 36264 to 36298).

This PCR fragment was digested with BamHI and HindIII and cloned into the vector pUC19 digested with the same restriction enzymes. The plasmid obtained was named pUC19-Ptrc01/OP01/RBS01-adhE2ca-TT02

To amplify the prpE gene, a PCR are carried out using chromosomal DNA of *E. coli* as template and the primers prpE F and prpE R.

prep F (SEQ ID NO 70):
tctagaggatccaagttcaacaggagagcattatg a region (bold underlined case) for the addition of the restriction sites XbaI and BamHI
a region homologous (lower case) to the region from 351910 to 351932 (http://ecogene.org/blast.php)

prep R_(SEQ ID NO 71):
ggatccgctagccctaggtacgtactactcttccatcgcctggc a region (bold underlined case) for the addition of the restriction sites BamHI, NheI, AvrII, SnaBII
a region (lower case) homologous to the region from 353816 to 353797 (http://ecogene.org/blast.php)

This PCR fragment was digested with XbaI and NheI and cloned into the vector pUC19-Ptrc01/OP01/RBS01-adhE2ca-TT02 digested with the same restriction enzymes.

The plasmid obtained was named pUC19-Ptrc01/OP01/RBS01-adhE2ca-prpE-TT02.

4.4 Construction of the MG1655 ΔsucCD ΔaceBAK ΔarcA ΔgdhA (pUC19-Ptrc01/OP01/RBS01-adhE2ca-prpE-TT02) (pME101-kivDll-yqhD-TT07) Strain The pUC19-Ptrc01/OP01/RBS01-adhE2ca-prpE-TT02 and the pME101-kivDll-yqhD-TT07 plasmids are then introduced into the strain MG1655 ΔsucCD ΔaceBAK ΔarcA ΔgdhA.

Example 5

Fermentation of Ethylene Glycol Producing Strains in Erlenmeyer Flasks

Performances of strains were assessed in 500 ml baffled Erlenmeyer flask cultures using modified M9 medium (Anderson, 1946, Proc. Natl. Acad. Sci. USA 32:120-128) that was supplemented with 10 g/l MOPS and 10 g/l glucose and adjusted at pH 6.8. Spectinomycin was added if necessary at a concentration of 50 mg/l and/or Chloramphenicol was added if necessary at a concentration of 30 mg/l. A 24 h preculture was used to inoculate a 50 ml culture to an OD600 nm of about 0.3. The cultures were kept on a shaker at 37° C. and 200 rpm until the glucose in the culture medium was exhausted. At the end of the culture, glucose and major products were analyzed by HPLC using a Biorad HPX 97H column for the separation and a refractometer for the detection. Production of Ethylene Glycol was confirmed by gas chromatography/mass spectrometry (GC/MS) with a Hewlett Packard 6890 Series gas chromatograph coupled to a Hewlett Packard 5973 Series mass selective detector (EI) and a HP-INNOWax column (25 m length, 0.20 mm i.d., 0.20 micron film thickness). The retention time and mass spectrum of Ethylene Glycol generated were compared to that of authentic Ethylene Glycol.

Comparison of the performances between the production strain and a reference strain is given in table below. (see below for the construction of the producing strain)

| Culture_ref | Strain_genotype | [ethylene glycol] (mM) |
|---|---|---|
| FbDI_0180 | MG1655 DpykF | nd |
| FbDI_0184 | MG1655 DpykF (pME101-kivDll-yqhD-yeaB-TT07) (pCC1BAC-serA) | 0.63 | nd: not detected

Example 6

Construction of Strain with Increased Ethylene Glycol Pathway Flux: MG1655 ΔpykF (pME101-kivDll-yqhD-yeaB-TT07) (pCC1BAC-serA)

6.1 Construction of a Plasmid for the Overexpression of the Hydroxy Keto-Acid Decarboxylase kivD of *Lactococcus lactis*, the Hydroxy Aldehyde Reductase yqhD and the Phosphohydroxy Pyruvate Phosphatase yeaB Genes of *Escherichia coli*: pME101-kivDll-yqhD-yeaB-TT07 Plasmid The yeaB containing fragment was restricted by XbaI and BglII and cloned into the vector pME101-kivDll-yqhD restricted by the same restriction enzymes, the resulting plasmid was named pME101-kivDll-yqhD-yeaB-TT07.

The yeaB gene was PCR amplified from genomic DNA of the E. coli MG1655 strain with the oligonucleotides yeaB F and yeaB R:

yeaB F
(SEQ ID NO 72)
AGC T*GTATAC*T*AGAATTCA*T*AGATCT*taaggaggtatattATGGAA

TACCGTAGCCTGACGC

- a region (italic bold upper case) for addition of a BstZ17I, EcoRI and BglII restriction sites
- a region (underlined lower case) for addition of a Ribosome Binding Site
- a region (upper case) homologous to the E. coli MG1655 yeaB region from 1894195 to 1894215 (reference sequence on the EcoGene website), yeaB R
(SEQ ID NO 73)
GCTTATAAGCCAGCTGGCTCTAGATAG<u>CAGAAAGGCCCACCCGAAGGT</u>

<u>GAGCCAGGAGTATACATGAAGCATTTCCGTTAATTAACGGAGCTCATC</u>

CTAGGTCAGGGTTTCACACCAATTTGCAGCGCC

- a region (bold upper case) homologous to the E. coli MG1655 yeaB region from 1894772 to 1894745 (reference sequence on the EcoGene),
- a region (underlined upper case) homologous to the terminator sequence T7Te (ref: Harrington K. J., Laughlin R. B. and Liang S. Proc Natl Acad Sci USA. 2001 Apr. 24; 98(9):5019-24):
- a region (italic upper case) for addition of a PsiI, PvuII, XbaI, BstZ17I, XmnI, PacI, SacI and AvrII restriction sites The PCR amplified fragment was cut with the restriction enzymes XbaI and BglII and cloned into the XbaI-BglII sites of the vector pME101-kivDll-yqhD-TT07 giving vector pME101-kivDll-yqhD-yeaB-TT07.

6.2 Construction of a Plasmid for Overexpression of the Phosphoglycerate Dehydrogenase serA of *Escherichia coli*: pCC1BAC-serA Plasmid To increase the expression of the serA gene, the gene was expressed from the copy control vector pCC1BAC (Epicentre) using its proper promoter.

For this purpose, the serA gene was amplified from the E. coli genome using the oligonucleotides serA F and serA R. The PCR product was restricted using enzymes XbaI and SmaI and cloned into the vector pUC18 (Stratagene) restricted by the same restriction enzymes. The resulting vector was named pUC18-serA.

serA F (SEQ ID NO 74):
ctagTCTAGATTAGTACAGCAGACGGGCGCG
with
- a region (upper case) homologous to the sequence (3055199-3055220) of the gene serA (reference sequence on the EcoGene website),
- a region (bold case) harbouring the XbaI site serA R (SEQ ID NO 75):
tccCCCGGGAAGCTTCCGTCAGGGCGTG-GTGACCG
with
- a region (upper case) homologous to the sequence (3056880-3056861) of the gene serA region (reference sequence on the EcoGene website),
- a region (bold case) harbouring the SmaI and HindIII sites To transfer the gene serA into the copy control vector pCC1BAC, the vector pUC18-serA was restricted with the enzyme HindIII and cloned into HindIII cloning ready pCC1BAC (Epicentre).

The resulting construct was verified and called pCC1BAC-serA.

6.3 Construction of the MG1655 ΔpykF (pME101-kivDll-yqhD-yeaB-TT07) (pCC1BAC-serA) Strain The MG1655 ΔpykF strain construction was previously detailed (part 2.2)

The pCC1BAC-serA and the pME101-kivDll-yqhD-yeaB-TT07 plasmids were then introduced into the strain MG1655 ΔpykF.

Example 7

Demonstration of the Hydroxy Keto-Acid Decarboxylase Activity Encoded by the Gene kivD of *Lactococcus lactis*

7.1 Construction of Strain for KivD Characterisation: BL21 (pPAL7-kivDll)

To characterise the KivD protein, the corresponding gene was expressed from the expression vector pPAL7 (Bio-rad).

For this purpose, the kivD gene was amplified from the *Lactococcus lactis* genome using the oligonucleotides pPAL7-kivDll F and pPAL7-kivDll R. The PCR product was restricted using enzymes HindIII and EcoRI and cloned into the vector pPAL7 restricted by the same restriction enzymes. The resulting vector was named pPAL7-kivDll.

pPAL7-kivDll F (SEQ ID NO 76):
ccc
<u>AAGCTT</u>tgACTTCTATGTATACCGTGGGTGATTATC
with
- a region (italic case) homologous to the sequence of the synthetic gene of the *Lactococcus lactis* kivD gene,
- a region (bold case) harbouring the nucleotides necessary to generate tag-free protein containing a short N-terminal amino acid extension to favour the purification
- a region (underlined case) harbouring the HindIII restriction site pPAL7-kivDll R (SEQ ID NO 77):
g<u>GAATTC</u>TTAGCTTTTATTCTGTTCGGCGAACAG
with
- a region (italic case) homologous to the sequence of the synthetic gene of the *Lactococcus lactis* kivD gene,
- a region (underlined case) harbouring the EcoRI restriction site The pPAL7-kivDll plasmid was then introduced into the strain BL21 (DE3) competent cells (Invitrogen).

7.2 Overproduction of the Protein KivD

The overproduction of the protein KivD was done in a 2 l Erlenmeyer flask, using LB broth (Bertani, 1951, J. Bacteriol. 62:293-300) that was supplemented with 2.5 g/l glucose and 100 mg/l of ampicillin. An overnight preculture was used to inoculate a 500 ml culture to an $OD_{600\,nm}$ of about 0.15. This preculture was carried out in a 500 ml Erlenmeyer flask filled with 50 ml of LB broth that was supplemented with 2.5 g/l glucose and 100 mg/l of ampicillin. The culture was first kept on a shaker at 37° C. and 200 rpm until $OD_{600\,nm}$ was about 0.5 and then the culture was moved on a second shaker at 25° C. and 200 rpm until $OD_{600\,nm}$ was 0.6-0.8 (about one hour), before induction with 500 μM IPTG. The culture was kept at 25° C. and 200 rpm until $OD_{600\,nm}$ was around 4, and then it was stopped. Cells were centrifuged at 7000 rpm, 5 minutes at 4° C., and then stored at −20° C.

7.3 Purification of the Protein KivD

7.3.1 Step 1: Preparation of Cell-Free Extracts.

About 188 mg of *E. coli* biomass was suspended in 30 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM $MgCl_2$ and 1UI/ml of DNaseI. Cells debris was removed by centrifugation at 12000 g for 30 min at 4° C.

7.3.2 Step 2: Affinity Purification

The protein was purified from crude cell-extract by affinity on a Profinity column (BIORAD, Bio-Scale Mini Profinity exact cartridge 5 ml) according to the protocol recommended by the manufacturer. Crude extract was loaded on a 5 ml Profinity exact cartridge equilibrated with 100 mM potassium phosphate pH 7.6. The column was washed with 10 column volumes of the same buffer and incubated overnight with 100 mM potassium phosphate pH 7.6, 100 mM fluoride at 4° C. The protein was eluted from the column with 2 column volumes of 100 mM potassium phosphate pH 7.6. The tag remained tightly bound to the resin and the purified protein was released. The fractions containing the protein were pooled and dialyzed against 100 mM potassium phosphate, 150 mM NaCl and 10% glycerol pH 8.

Protein concentration was measured using the Bradford protein assay.

7.4 Hydroxy Keto-Acid Decarboxylase Assay

7.4.1 Chemical synthesis of 5-hydroxy-2-ketopentanoic acid

Chemical synthesis of 5-hydroxy-2-ketopentanoic acid has been described in the publication:

Friedhelm Korte, Karl Heinz Büchel, α-Hydroxyalkyliden-lacton-Umlagerung, X. α-Hydroxyalkyliden-lacton-Umlagerung in wäβriger Salzsäure *Chemische Berichte*, Volume 92 Issue 4, Pages 877-883 (1959)

7.4.2 Chemical Synthesis of 4-hydroxy-2-ketobutyric Acid

Chemical synthesis of 4-hydroxy-2-ketobutyric acid has been described in the publication: R S Lane; EE Dekker; (1969). 2-keto-4-hydroxybutyrate. Synthesis, chemical properties, and as a substrate for lactate dehydrogenase of rabbit muscle Biochemistry., 8 (7), 2958-2966.

7.4.3 Hydroxy Keto-Acid Decarboxylase Assay

The decarboxylation of hydroxy keto-acids was measured at 30° C. using a coupled enzymatic assay. The hydroxy keto-acid decarboxylase activity assay was carried out with 50 mM potassium phosphate buffer pH 6, 0.2 mM NADH, 1 mM $MgSO_4$, 0.5 mM thiamin diphosphate, 72 units/ml alcohol dehydrogenase from *Saccharomyces cerevisiae*, 10 mM hydroxy keto-acid neutralized (Hydroxypyruvic acid or 4-hydroxy-2-ketobutyric acid or 5-hydroxy-2-ketopentanoic acid) and about 40 μg of purified protein in a total volume of 1 ml. The consumption of NADH was monitored at 340 nm on a spectrophotometer. The activity detected in control assay, lacking the substrate, was subtracted from the activity detected in the assay with substrate. A unit of hydroxy keto-acid decarboxylase activity is the amount of enzyme required to catalyze the decarboxylation of 1 mmol of hydroxy keto-acid per min at 30° C. (Epsilon 340 nm=6290 $M^{-1}$ $cm^{-1}$)

7.5 Activity of Purified Enzyme

| | Activity of purified enzyme (mUI/mg) |
|---|---|
| Hydroxypyruvate decarboxylase assay | 79 |
| 4-hydroxy-2-ketobutyrate decarboxylase assay | 70 |
| 5-hydroxy-2-ketopentanoate decarboxylase assay | 63 |

Example 8

Demonstration of the Hydroxy Aldehyde Reductase Activity Encoded by the Gene yqhD of *Escherichia coli*

8.1 Construction of a Strain for yqhD Characterisation: MG1655 ΔpykF::Km (pTRC99A-yqhD)

8.1.1 Construction of Strain MG1655 ΔyqhD::Km

To delete the yqhD gene, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used:

ΔyqhDF (SEQ ID NO 78)
atgaacaactttaatctgcacac-
cccaacccgcattctgrttggtaaag-
gcgcaatcgctggtttacgcgaacaaattccgtgtaggctggagctgcttcg
with
  a region (lower case) homologous to the sequence (3153377 to 3153456) of the yqhD region (reference sequence on the EcoGene website),
  a region (upper case) for the amplification of the kanamycin resistance cassette (reference sequence in Datsenko, K. A. & Wanner, B. L., 2000, PNAS, 97: 6640-6645), ΔyqhDR (SEQ ID NO 79)
ttagcgggcggcttcgtatatacggcg-
gctgacatccaacgtaatgtcatgattttcgcccagttgggtcatgccgtgctcc
catatgaatatcctccttag
with
  a region (upper case) homologous to the sequence (3154540 to 3154460) of the yqhD region (reference sequence on the EcoGene website),
  a region (upper case) for the amplification of the kanamycin resistance cassette (reference sequence in Datsenko, K. A. & Wanner, B. L., 2000, PNAS, 97: 6640-6645).

The oligonucleotides ΔyqhDF and ΔyqhDR are used to amplify the kanamycin resistance cassette from the plasmid pKD4. The PCR product obtained is then introduced by electroporation into the strain MG 1655 (pKD46). The kanamycin resistant transformants are then selected and the insertion of the resistance cassette is verified by a PCR analysis with the oligonucleotides yqhDF and yqhDR defined below. The strain retained is designated MG1655 ΔyqhD::Km. yqhDF (SEQ ID NO 80): ggcgtctcgccatacaacaaacgcacatcgggc (homologous to the sequence from 3153068 to 3153100). yqhDR (SEQ ID NO 81): gggctttgccgacaccttcttcgttcttg (homologous to the sequence from 3154825 to 3154797).

8.1.2 Construction of Plasmid pTRC99A-yqhD

To characterise the YqhD protein, the corresponding gene was expressed from the vector pTRC99A (Amersham).

For this purpose, the yqhD gene was amplified from the *E. coli* genome using the oligonucleotides yqhD F pTRC99A F and yqhD R pTRC99A R. The PCR product was restricted using enzymes HindIII and BspHI and cloned into the vector pTRC99A restricted by the NcoI-HindIII restriction enzymes. The resulting vector was named pTRC99A-yqhD.

yqhD F pTRC99A F (SEQ ID NO 82):

cgatgcacgtc<u>atgaacaactttaatctgcacaccccaacccg</u>, with:
- a region (underlined case) homologous to the sequence (3153377 to 3153408) of the gene yqhD (reference sequence on the EcoGene website),
- a BspHI restriction site (bold case)

yqhD R pTRC99A R (SEQ ID NO 83):

ggcgtaaaaagcttagcgggcggcttcgtatatacggcggctgacatccaacgtaatgtcgtgattttcg with:
- a region (underlined case) homologous to the sequence (3154540 to 3154483) of the gene yqhD (reference sequence on the EcoGene website),
- a HindIII restriction site (bold case)

The pTRC99A-yqhD plasmid was then introduced into the strain MG1655 ΔyqhD::Km.

8.2 Overproduction of the Protein YqhD

The protein YqhD was overproduced at 37° C. under aerobic conditions in 2 l baffled Erlenmeyer flasks with 500 ml LB medium with 2.5 g/l glucose and 50 mg/l of ampicillin and 50 mg/l of kanamycin. The flasks were agitated at 200 rpm on an orbital shaker. When the optical density measured at 550 nm reached 0.5 units, the flasks were incubated at 25° C. When the optical density reached 1.2 units, the production of YqhD proteins was induced by adding IPTG to a final concentration of 500 µM. The biomass was harvested by centrifugation when the cultures reached an optical density above 3.5 units. The supernatant was discarded and the pellet was stored at −20° C. before use.

8.3 Purification of the Protein YqhD

8.3.1 Step 1: Preparation of Cell-Free Extracts.

400 mg of *E. coli* biomass were suspended in 70 ml of 50 mM Hepes pH 7.5, and a protease inhibitor cocktail. Cells were sonicated on ice (Branson sonifier, 70 W) in a Rosett cell RZ3 during eight cycles of 30 sec with 30 sec intervals. After sonication, cells were incubated for 1 hour at room temperature with 1 mM MgCl2 and 1 UI/ml of DNaseI. Cells debris was removed by centrifugation at 12000 g for 30 min at 4° C. The supernatant was kept as the crude extract.

8.3.2 Step 2: Ammonium Sulphate Precipitation

The crude extract was precipitated at a concentration of 50% ammonium sulphate: solid ammonium sulphate (300 g/l) was added to the crude extract on ice. After 15 min of incubation at 4° C., the mix was centrifuged at 12000 g for 15 min at 4° C. The supernatant was discarded and the precipitate dissolved in 50 ml of 50 mM Hepes pH 7.5, 1 M ammonium sulphate.

8.3.3 Step 3: Hydrophobic Chromatography.

Using an Akta Purifier (GE Healthcare), the protein extract from the previous step was loaded onto a 5 ml HiTrap PhenylHP column (GE Healthcare) equilibrated with the same buffer. The column was washed with 10 column volumes of the same buffer. Proteins were eluted with two step gradients, a gradient of 10 column volumes from 1 M to 0.5 M ammonium sulphate and a gradient of 20 column volumes from 0.5 M to 0 M ammonium sulphate. After elution, the column was washed with 10 column volumes of 50 mM Hepes pH 7.5. The flow rate of the column was 2.5 ml/min and 2.5 ml fractions were collected.

The fractions which contain the protein were pooled, dialyzed in 50 mM Hepes pH 7.5 and concentrated to a concentration of 1.14 µg/µl.

8.4 Hydroxy Aldehyde Reductase Assays

8.4.1 Chemical synthesis of 4-hydroxybutyraldehyde

Chemical synthesis of 4-hydroxybutyraldehyde has been described in the publication: No 158 Transposition des dihydro-2.5 furannes en dihydro-2.3 furannes. —Application à la préparation de l'hydroxy-4 butanal; par R. PAUL, M. FLUCHAIRE et G. GOLLARDEAU.

Bulletin de la Société Chimique de France, 668-671, 1950.

8.4.2 Glycolaldehyde and 4-hydroxybutyraldehyde Reductase Activity Assay

Glycolaldehyde and 4-hydroxybutyraldehyde reductase activity was assayed by measuring the initial rate of NADPH oxidation with a spectrophotometer at a wavelength of 340 nm and at a constant temperature of 30° C. The reaction mixture using glycolaldehyde or 4-hydroxybutyraldehyde as substrate was carried out in 20 mM Hepes pH 7.5, 0.1 mM Zinc sulphate, 0.2 mM NADPH, 2 µg of purified enzyme in a final volume of 1 ml. The reaction mixture was incubated for 5 min at 30° C. and then the reaction was initiated by the addition of the substrate (glycolaldehyde or 4-hydroxybutyraldehyde) at a final concentration of 10 mM. A control assay (blank), lacking the substrate, was run in parallel and the value measured for the control was subtracted from the value measured for the assay to take into account non-specific oxidation of NADPH. (Epsilon 340 nm=6290 M−1 cm−1).

One unit of enzyme activity was defined as the amount of enzyme that consumed 1 µmol substrate per minute under the conditions of the assay. Specific enzyme activity was expressed as units per mg of protein.

8.4.3 3-hydroxypropionaldehyde Reductase Activity Assay

The activity of YqhD toward the substrate 3-hydroxypropionaldehyde (3-HPA) has been described in the publication: Hongmei Li; Jia Chen; Hao Li; Yinghua Li; Ying Li; (2008). Enhanced activity of yqhD oxidoreductase in synthesis of 1,3-propanediol by error-prone PCR Prog Nat. Sci., 18 (12), 1519-1524.

These authors have used 5 mM Zinc chloride, 1 mM EDTA and 1 mM Beta-mercaptoethanol for their 3-hydroxypropionaldehyde reductase assays.

8.5 Activity of Purified Enzyme

|  | Activity of purified enzyme (mUI/mg) |
|---|---|
| Glycoladehyde reductase activity assay | 9840 |
| 3-hydroxypropionaldehyde reductase activity assay | 7918 |
| 4-hydroxybutyraldehyde reductase activity assay | 1443 |

Example 9

Demonstration of the L-Serine Transaminase and L-Homoserine Transaminase Activity Encoded by the Gene serC of *Escherichia coli*

9.1 Construction of Strain for SerC Characterisation: BL21 (pPAL7-serC)

To characterise the SerC protein, the corresponding gene was expressed from the expression vector pPAL7 (Bio-rad).

For this purpose, the serC gene was amplified from the *E. coli* genome using the oligonucleotides pPAL7-serC F and pPAL7-serC R. The PCR product was restricted using enzymes HindIII and EcoRI and cloned into the vector pPAL7 restricted by the same restriction enzymes. The resulting vector was named pPAL7-serC.

pPAL7-serC F (SEQ ID NO 84):
ccc AAGCTTtgATGGCTCAAATCTTCAATTTTAGTTCTGG
with
- a region (bold case) homologous to the sequence (956876-956904) of the gene serC (reference sequence on the EcoGene website),
- a region (underlined case) harbouring the HindIII restriction site pPAL7-serC R (SEQ ID NO 85):
gGAATTCTTAACCGTGACGGCGTTCGAACTCA ACC
with
- a region (bold case) homologous to the sequence (957964-957937) of the gene serC region (reference sequence on the EcoGene website),
- a region (underlined case) harbouring the EcoRI restriction site The pPAL7-serC plasmid was then introduced into competent BL21 (DE3) cells (Invitrogen).

9.2 Overproduction of the Protein SerC

The overproduction of the protein SerC was done applying the same protocol as example #7.2

9.3 Purification of the Protein SerC 9.3.1 Step 1: Preparation of Cell-Free Extracts About 280 mg of *E. coli* biomass was suspended in 45 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and 1 UI/ml of DNaseI. Cells debris was removed by centrifugation at 12000 g for 30 min at 4° C.

9.3.2 Step 2: Affinity Purification

The protein was purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated 30 min with 100 mM potassium phosphate pH 7.6, 100 mM fluoride at room temperature. The protein was eluted from the column with 2 column volumes of 100 mM potassium phosphate pH 7.6. The tag remained tightly bound to the resin and the purified protein was released. The fractions containing the protein were pooled and dialyzed against 100 mM Tris HCl, 150 mM NaCl and 10% glycerol pH 8.

Protein concentration was measured using the Bradford protein assay.

9.4 L-Serine Transaminase Activity Assay

For the L-serine transaminase activity assay about 30 μg of purified enzyme was added to a buffer containing 50 mM Tris-HCl buffer pH 8.2, 3 mM L-Serine, 1 mM α-ketoglutaric acid in a total volume of 300 μl. The reaction was incubated during 60 min at 30° C. The reaction product (hydroxypyruvic acid) was measured directly by LC-MS/MS.

9.5 L-homoserine Transaminase Assay

The L-homoserine transaminase activity was measured at 30° C. using a coupled enzymatic assay. The L-homoserine transaminase activity assay was carried out with 420 mM potassium phosphate buffer pH 8.2, 2 mM acetylpyridine adenine dinucleotide, 3 mM L-homoserine, 20 units/ml glutamic dehydrogenase from bovine liver, 1 mM alpha-ketoglutaric acid neutralized and about 50 μg of crude extract in a total volume of 1 ml. The consumption of acetylpyridine adenine dinucleotide was monitored at 375 nm on a spectrophotometer. The activity detected in control assay, lacking the substrate (L-homoserine), was subtracted from the activity detected in the assay with substrate. A unit of L-homoserine transaminase activity is the amount of enzyme required to catalyze the transamination of 1 μmol of L-homoserine per min at 30° C. (Epsilon 375 nm=6100 M−1 cm−1)

9.6 Activities of Purified Enzyme

|  | Activity of purified enzyme (mUI/mg) |
| --- | --- |
| L-Serine transaminase assay | 186 |
| L-Homoserine transaminase assay | 118 |

Example 10

Demonstration of the 3-phosphohydroxypyruvate Phosphatase Activity Encoded by the Gene GPP2 of *Saccharomyces cerevisiae*

10.1 Construction of a Strain for GPP2sc Characterization: BL21 (pPAL7-gpp2sc)

To characterise the GPP protein, the corresponding gene is expressed from the expression vector pPAL7 (Bio-rad).

For this purpose, the gpp gene is amplified from the *Saccharomyces cerevisiae* genome using the oligonucleotides pPAL7-gpp2sc F and pPAL7-gpp2sc R. The PCR product is restricted using enzymes HindIII and BamHI and cloned into the vector pPAL7 restricted by the same restriction enzymes. The resulting vector is named pPAL7-gpp2sc. pPAL7-gpp2sc F (SEQ ID NO 86):
ccc AAGCTTTgATGGGATTGACTACTAAACCTCTATC
with
- a region (bold case) homologous to the sequence (280680-280655) of the gene gpp2 region (reference sequence on the *Saccharomyces* Genome Database website),
- a region (underlined case) harbouring the HindIII restriction site pPAL7-kivDll R (SEQ ID NO 87):
gGGATCCTTACCATTTCAACAGATCGTCCTTAGC
with
- a region (bold case) homologous to the sequence (279928-279954) of the gene gpp2 region (reference sequence on the *Saccharomyces* Genome Database website),
- a region (underlined case) harbouring the BamHI restriction site The pPAL7-gpp2sc plasmid is then introduced into competent BL21 (DE3) cells (Invitrogen).

10.2 Overproduction of the Protein GPP2sc

The overproduction of the protein GPP2sc was done applying the same protocol as example #7.2

10.3 Purification of the Protein GPP2sc 10.3.1 Step 1: Preparation of Cell-Free Extracts.

About 294 mg of *E. coli* biomass was suspended in 45 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and 1 UI/ml of DNaseI. Cells debris was removed by centrifugation at 12000 g for 30 min at 4° C.

10.3.2 Step 2: Affinity Purification

The protein was purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated overnight with 100 mM potassium phosphate pH 7.6, 100 mM fluoride at room temperature. The protein was eluted from the column with 2 column volumes of 100 mM potassium phosphate pH 7.6.

The tag remained tightly bound to the resin and the purified protein was released. The fractions containing the protein were pooled and dialyzed against 100 mM potassium phosphate, 150 mM NaCl, 10% glycerol pH 8 and concentrated to a concentration of 0.22 µg/µl.

Protein concentration was measured using the Bradford protein assay.

10.4 3-phosphohydroxypyruvate Phosphatase Activity Assay

10.4.1 Chemical synthesis of 3-phosphohydroxypyruvate

Chemical synthesis of 3-phosphohydroxypyruvate has been described in the publication: C E Ballou; H Hesse; R Hesse; (1956). The Synthesis and Properties of Hydroxypyruvic Acid Phosphate J Am Chem. Soc., 78 (15), 3718-3720.

10.4.2 3-Phosphohydroxypyruvate Phosphatase Activity Assay 3-phosphohydroxypyruvate phosphatase activity assay was carried out with 50 mM Tris-HCl buffer pH 8.2, 5 mM $MgCl_2$, 3.6 mM 3-phosphohydroxypyruvate and about 6 µg of purified enzyme (Gpp) in a total volume of 300 µl. The reaction was incubated during 120 min at 30° C. The reaction product (hydroxypyruvic acid) was measured directly by LC-MS/MS.

10.5 Activity of Purified Enzyme

|  | Activity of purified enzyme (mUI/mg) |
|---|---|
| 3-phosphohydroxypyruvate phosphatase assay | 9 |

Example 11

Simulation of Maximum Yields for Ethylene Glycol, 1,3-propanediol and 1,4-butanediol Production

11.1 Parameters Used for Simulations

Simulations have been performed with our METEX proprietary software METOPT™. A simplified metabolic network of *E. coli* has been used including a central metabolic network, metabolic pathways for all biomass precursors and specific production pathways as described above. A classical biomass composition for *E. coli* has been used. For each specific diol, two simulations have been performed. The first one to calculate a theoretical maximum yield (taking into account only stoichiometry of the model, with no growth and no maintenance energy). The second one to calculate a practical maximum yield, taking into account a growth rate of 0.1 $h^{-1}$ and a maintenance energy of 5 $mmol_{ATP} \cdot g_{DW}^{-1} \cdot h^{-1}$. All simulations have been performed with a specific uptake rate of glucose of 3 $mmol \cdot g_{DW}^{-1} \cdot h^{-1}$. For ethylene glycol and 1,3-propanediol, simulations have been performed in aerobic conditions. Specifically for 1,4-butanediol, simulations have been performed both in aerobic and anaerobic conditions. For anaerobic conditions, the growth rate could not be imposed to 0.1 $h^{-1}$. The growth rate is the maximal growth rate attainable according to available ATP.

11.2 Simulations Results

|  | Ethylene glycol | 1,3-propanediol | 1,4-butanediol (aerobic) | 1,4-butanediol (anaerobic) |
|---|---|---|---|---|
| Maximum theoretical yield (g/g) | 0.69 | 0.60 | 0.50 | 0.50 |
| Maximum practical yield (g/g) | 0.50 | 0.39 | 0.35 | 0.45 ($\mu_{max} = 0.03\ h^{-1}$) |

Example 12

Construction of Strains with Increased 1.3-propanediol Pathway Flux and Expressing a 2-keto Acid Decarboxylase Encoding Gene and an Hydroxy Aldehyde Reductase Encoding Gene MG1655 ΔpykF ΔmetA ΔthrLABC (pBBR1MCS5-Ptrc01/RBS01*2-yqhD-kivDll-TT07) (pME101-thrA*1-serC)

12.1 Construction of Strain MG1655 ΔpykF

To delete the pykF gene, the homologous recombination strategy described by Datsenko and Wanner (2000, PNAS, 97: 6640-6645) was used. The construction was performed as described in the previous example 2.2

The kanamycin resistance cassette was eliminated. The plasmid pCP20 carrying FLP recombinase acting at the FRT sites of the kanamycin resistance cassette was then introduced into the recombinant sites by electroporation. After a series of cultures at 42° C., the loss of the kanamycin resistance cassettes was verified by a PCR analysis with the same oligonucleotides as used previously (pykFF/pykFR). The strain retained was designated MG1655 ΔpykF.

12.2 Construction of Strain MG1655 ΔpykF ΔmetA

To delete the metA gene, the homologous recombination strategy described by Datsenko & Wanner (2000) was used. The construction was performed as described in the previous example 3.1.

The strain retained was designated MG1655 ΔpykF ΔmetA.

12.3 Construction of Strain MG1655 ΔpykF ΔmetA ΔthrLABC

To delete the thrLABC operon, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used. DthrLABF (SEQ ID NO 88:

cgggcaatatgtctctgtgtggat-
taaaaaaagagtgtctgatagcagcttctgaactggttacc
ttcctggctcaccttcgggtgggcctttctggtatacTGTAGGCTGG
AGCTGCTTCG with a region (lower case) homologous to the sequence (22-86) of the thrLABC region (reference sequence on the EcoGene website), a region (bold underlined lower case) for T7Te transcriptional terminator sequence from T7 phage (Harrington K. J., Laughlin R. B. and Liang S. Proc Natl Acad Sci USA. 2001 Apr. 24; 98(9):5019-24), a region (upper case) for the amplification of the chloramphenicol resistance cassette (reference sequence in Datsenko, K. A. & Wanner, B. L., 2000, PNAS, 97: 6640-6645), DthrLABCR (SEQ ID NO 89):

CCCTGTCATTTTTCTCCATAATTTCT-
TCATAAAAAAGCCGGGCTGCATAAAAGC AAAC-
CCGGCCTGATTGAGATAATGAATAGATT
CCCGGGGGAGGCGCCCGCGGATCCCATATGAA
TATCCTCCTTAG with a region (upper case) homologous to the sequence (5106-5021) of the thrLABC region (reference sequence on the EcoGene website), a region (italic upper case) for addition of a BamHI-SfoI-SmaI restriction sites a region (bold upper case) for the amplification of the chloramphenicol resistance cassette.

The oligonucleotides ΔthrBF and ΔthrCR were used to amplify the chloramphenicol resistance cassette from the plasmid pKD3. The PCR product obtained was then introduced by electroporation into the strain MG1655 (pKD46). The chloramphenicol resistant transformants were then selected and the insertion of the resistance cassette was verified by a PCR analysis with the oligonucleotides thrLF and thrCR defined below. The strain retained was designated MG1655 ΔthrLABC::Cm.

thrLF (SEQ ID NO 90): GCCATGCCGCGCTGGT-GTTTGGTCGCG (homologous to the sequence from 4639281 to 4639307). thrCR (SEQ ID NO 91): GCGACCA-GAACCAGGGAAAGTGCG (homologous to the sequence from 5283 to 5260).

To transfer the ΔthrLABC::Cm, the method of phage P1 transduction was used. The preparation of the phage lysate of the strain MG1655 ΔthrLABC::Cm was used for the transduction into the strain MG1655 ΔpykF ΔmetA. The chloramphenicol resistant transformants were then selected and the ΔthrLABC::Cm was verified by a PCR analysis with the previously defined oligonucleotides thrLF and thrCR. The strain retained was designated MG1655 ΔpykF ΔmetA ΔthrLABC::Cm.

The chloramphenicol resistance cassette was eliminated. The plasmid pCP20 carrying FLP recombinase acting at the FRT sites of the chloramphenicol resistance cassettes was then introduced into the recombinant sites by electroporation. After a series of cultures at 42° C., the loss of the chloramphenicol resistance cassette was verified by a PCR analysis with the same oligonucleotides as used previously ((pykFF/pykFR, metAF/metAR, and thrLF/thrCR). The strain retained was designated MG 1655 ΔpykF ΔmetA ΔthrLABC.

12.4 Construction of a Plasmid for Overexpression of the L-homoserine Transaminase serC of Escherichia coli: pME101-thrA*1-serC Plasmid To increase the expression of the serC gene, the gene was expressed from the pME101-thrA*1 previously described (PCT_WO2008707041) using its proper promoter.

For this purpose, the serC gene was amplified from the E. coli genome using the oligonucleotides serC F and serC R.

The PCR product was restricted using enzymes XbaI and SmaI and cloned into the vector pME101-thrA*1 restricted by the same restriction enzymes. The resulting vector was named pME101-thr A*1-serC.

serC F (SEQ ID NO 92):
TGCTCTAGAGTCCGCGCTGTGCAAATC-
CAGAATGG with a region (upper case) homologous to the sequence (956619-956644) of the gene serC (reference sequence on the EcoGene website), a region (bold upper case) harbouring the XbaI site serC R (SEQ ID NO 93):

CCCAAGCTTAACTCTCTACAACAGAAATAAAAAC with a region (upper case) homologous to the sequence (958028-958004) of the gene serC region (reference sequence on the EcoGene website), a region (bold upper case) harbouring the HindIII site The PCR amplified fragment was cut with the restriction enzymes XbaI and HindIII and cloned into the XbaI-HindIII sites of the vector pME101-thrA*1 giving vector pME101-thrA*1-serC.

12.5 Construction of a Plasmid for the Overexpression of the Hydroxy Aldehyde Reductase yqhD Gene of *Escherichia coli* and the Alpha-Ketoisovalerate Decarboxylase kivD Gene of *Lactococcus lactis*: pBBR1MCS5-Ptrc01/RBS01*2-yqhD-kivDll-TT07 Plasmid The pME101-yqhD-kivDll-TT07 plasmid was first constructed. The kivDll gene from the pME101-kivDll-TT07 vector (PCT/2009/067994) restricted by BsrBI and BglII was cloned into the pME101VB01-yqhD vector (previously described in PCT/2007/000509) restricted by SnaBI and BglII, the resulting plasmid was named pME101-yqhD-kivDll-T07. The yqhD and kivDll genes were then PCR amplified from the pME101-yqhD-kivDll-T07 plasmid with the oligonucleotides Ptrc01-RBS01-yqhD pBBR F and kivD pBBR R. The PCR product was digested with the restriction enzymes SpeI and SmaI and cloned into the vector pBBR1MCS5 (M. E. Kovach, (1995), Gene 166:175-176) restricted by the same enzymes, giving the pBBR1MCS5-Ptrc01/RBS01*2-yqhD-kivDll-TT07 vector.

Ptrc01-RBS01-yqhD pBBR F (SEQ ID NO 94)
AgaACTAGTgagctgttgacaattaat-
catccggctcgtataatgtgtggaagtcgacGGATCC
taaggaggttataaatgaacaactttaatctgcacacccc a region (bold upper case) for addition of a SpeI restriction site a region (bold lower case) for addition of the constitutive Ptrc promoter sequence a region (italic upper case) for addition of a BamHI restriction site a region (underlined lower case) for addition of the Ribosome Binding Site sequence a region (italic lower case) homologous to the sequence (3153377-3153402) of the MG1655 yqhD gene (on the EcoGene website)

kivD pBBR R (SEQ ID NO 95)
GAGCCCGGG
GCAGAAAGGCCCACCCGAAGGTGAGCCAGTGTGA
TACGTAGAA TTCTTAATTAAGTTAGCTTTTATTCTGT-
TCGGCG a region (bold italic upper case) for addition of a SmaI restriction site a region (underlined upper case) for T7Te transcriptional terminator sequence from T7 phage (Harrington K. J., Laughlin R. B. and Liang S. Proc Natl Acad Sci USA. 2001 Apr. 24; 98(9):5019-24), a region (bold upper case) for addition of a SnaBI-EcoRI-PacI restriction sites a region (italic upper case) homologous to the end of the synthetic kivD gene 12.6 Construction of Strain MG1655 ΔpykF ΔmetA ΔthrLABC (pME101-thrA*1-serC) (pBBR1MCS5-Ptrc01/RBS01*2-yqhD-kivDll-TT07)

The pME101-thrA*1-serC and pBBR1MCS5-Ptrc01/RBS01*2-yqhD-kivDll-TT07 plasmids were then introduced into the strain MG1655 ΔmetA ΔpykF ΔthrLABC.

12.7 Culture for 1,3-propanediol Production

Performances of strains were assessed in 500 ml baffled Erlenmeyer flask cultures using modified M9 medium (Anderson, 1946, Proc. Natl. Acad. Sci. USA 32:120-128) that was supplemented with 4.5 mM threonin, 5 mM methionin, 10 g/l MOPS and 10 g/l glucose and adjusted at pH 6.8. Spectinomycin and gentamycin were added at a concentration of 50 mg/l. 100 μM IPTG was also added for induction of the expression vector pME101. A 24 hours preculture was used to inoculate a 50 ml culture to an $OD_{600\,nm}$ of about 0.1.

The cultures were kept on a shaker at 37° C. and 200 rpm until the glucose in the culture medium was exhausted. At the end of the culture, glucose and major products were analyzed by HPLC using a Biorad HPX 97H column for the separation and a refractometer for the detection. Production of 1,3-propanediol was confirmed by LC/MS/MS.

The performances of different strains are given in table below.

| Culture_ref | Strain_ref | Genotype | [1,3-PDO] (mM) |
|---|---|---|---|
| FbDI335 FbDI340 FbDI357 | DI0084c02 | MG1655 ΔpykF ΔmetA ΔthrLABC | nd |
| FbDI336 FbDI341 FbDI358 FbDI395 | DI0107c01 | (MG1655 ΔpykF ΔmetA ΔthrLABC (pME101-thrA*1-serC) (pBBR1MCS5-Ptrc01/RBS01*2-yqhD-kivDll-TT07) | 0.391 +/− 0.125 | nd: not detected

The invention claimed is:

1. An *E. coli* microorganism genetically modified for the bioproduction of an aliphatic diol, wherein
the microorganism comprises a metabolic pathway for the decarboxylation of a hydroxy-2-keto-aliphatic acid metabolite with an enzyme having a 2-keto acid decarboxylase activity encoded by the gene kivD from *L. lactis*, the product obtained from said decarboxylation step being further reduced into the corresponding aliphatic diol with an enzyme having hydroxyl aldehyde reductase activity encoded by the gene yqhD from *E. coli*, and
the microorganism is genetically modified for the improved production of said hydroxy-2-keto-aliphatic acid metabolite by an increase of the homoserine transaminase activity or the homoserine oxidase activity encoded by SerC from *E. coli*.

2. The microorganism of claim 1, wherein the aliphatic diol is ethylene-glycol and the hydroxy-2-keto-aliphatic acid metabolite is hydroxypyruvate.

3. The microorganism of claim 1, wherein the aliphatic diol is 1,3-propanediol and the hydroxy-2-keto-aliphatic acid metabolite is 4-hydroxy-2-ketobutyrate.

4. The microorganism of claim 1, wherein the aliphatic diol is 1,4-butanediol and the hydroxy-2-keto-aliphatic acid metabolite is 5-hydroxy-2-ketopentanoate.

5. A method for the fermentative production of an aliphatic diol, comprising the steps of:
   culturing the microorganism of claim 1 on an appropriate culture medium comprising a source of carbon and
   recovering the aliphatic diol from the culture medium.

6. The method of claim 5, wherein the diol is further purified.

7. The method of claim 5, wherein the source of carbon is selected from the group consisting of: hexoses, pentoses, monosaccharides, disaccharides, oligosaccharides, molasses, starch and combinations thereof.

8. The method of claim 7, wherein the source of carbon is selected among glucose and sucrose.

\* \* \* \* \*

```
SEQUENCE LISTING

<160> NUMBER OF SEQ ID NOS: 95

<210> SEQ ID NO 1
<211> LENGTH: 26
<212> TYPE: DNA
<213> ORGANISM: Artificial Sequence
<220> FEATURE:
<223> OTHER INFORMATION: Restriction sites

<400> SEQUENCE: 1
ggatccatgc aagcttatgc gatatc                                      26

<210> SEQ ID NO 2
<211> LENGTH: 57
<212> TYPE: DNA
<213> ORGANISM: Artificial Sequence
<220> FEATURE:
<223> OTHER INFORMATION: Ptrc01 promoter

<400> SEQUENCE: 2
gagctgttga caattaatca tccggctcgt ataatgtgtg gaataaggag gtataac     57

<210> SEQ ID NO 3
<211> LENGTH: 1647
<212> TYPE: DNA
<213> ORGANISM: Artificial Sequence
<220> FEATURE:
<223> OTHER INFORMATION: Gene optimized for E. coli

<400> SEQUENCE: 3
atgtataccg tgggtgatta tctgctggat cgtctgcatg aactgggcat tgaagaaatt     60
ttcggcgttc cgggtgatta taatctgcag tttctggatc agattattag ccataaagat    120
atgaaatggg tgggtaatgc caatgaactg aatgcaagct atatgcaga tggttatgcc    180 cgtaccaaaa aagcagcagc atttctgacc acctttggtg ttggtgaact gagcgcagtt    240
aatggtctgg ctggtagcta tgcagaaaat ctgccggttg ttgaaattgt tggtagcccg    300
accagcaaag ttcagaatga aggcaaattt gtgcatcata ccctggccga tggtgatttt    360
aaacatttca tgaaatgca tgaaccggtt accgcagcac gtaccctgct gaccgcagaa    420
aatgcaaccg ttgaaattga tcgtgttctg agcgcactgc tgaaagaacg taaaccggtg    480
```

```
tatattaatc tgccggtgga tgttgcagca gcaaaagcag aaaaaccgag cctgccgctg      540
aaaaaagaaa atagcaccag caataccagc gatcaggaaa ttctgaataa aattcaggaa      600
tccctgaaaa acgccaaaaa accgattgtg attaccggtc atgaaattat tagctttggc      660
ctggaaaaaa ccgttaccca gtttattagc aaaaccaaac tgccgattac caccctgaat      720
tttggtaaaa gcagcgttga tgaagcactg ccgagctttc tgggtattta atggcacc        780 ctgagcgaac cgaatctgaa agaatttgtg gaaagcgcag atttcattct gatgctgggt      840
gttaaactga ccgatagctc taccggtgca tttacccatc atctgaatga aaacaaaatg      900
attagcctga atattgatga aggcaaaatt tttaatgaac gcattcagaa ttttgatttt      960
gaaagcctga ttagcagcct gctggatctg agcgaaatcg aatataaagg caaatatatt     1020
gataaaaaac aggaagattt tgttccgagc aatgcactgc tgtctcagga tcgtctgtgg     1080
caggcagttg aaaatctgac ccagagcaat gaaaccattg ttgcagaaca gggcaccagc     1140
ttttttggtg caagcagcat ttttctgaaa agcaaaagcc atttttattgg tcagccgctg     1200 tggggtagca ttggttatac ctttccggca gcactgggta gccagattgc agataaagaa     1260
agccgtcatc tgctgtttat tggtgatggt agcctgcagc tgaccgttca ggaactgggt     1320
ctggccattc gcgaaaaaat taatccgatt tgctttatta tcaataatga tggctatacc     1380
gtggaacgtg aaattcatgg tccgaatcag agctataatg atattccgat gtggaattat     1440
agcaaactgc cggaatcttt tggtgcaacc gaagatcgtg ttgtgagcaa aattgtgcgc     1500
accgaaaatg aatttgtgag cgtgatgaaa gaagcacagg cagatccgaa tcgtatgtat     1560
tggattgaac tgattctggc caaagaaggt gcaccgaaag ttctgaaaaa aatgggcaaa     1620
ctgttcgccg aacagaataa aagctaa                                         1647

<210> SEQ ID NO 4
<211> LENGTH: 46
<212> TYPE: DNA
<213> ORGANISM: Artificial Sequence
<220> FEATURE:
<223> OTHER INFORMATION: Terminator sequences

<400> SEQUENCE: 4
attacgtaga agatcttcct ggctcacctt cgggtgggcc tttctg                    46

<210> SEQ ID NO 5
<211> LENGTH: 27
<212> TYPE: DNA
<213> ORGANISM: Artificial Sequence
<220> FEATURE:
<223> OTHER INFORMATION: Restriction sites

<400> SEQUENCE: 5
ccccgggatg cggatccatg cgaattc                                         27

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide

<400> SEQUENCE: 6
ccgacagtaa gacgggtaag cctg                                            24

<210> SEQ ID NO 7
```

```
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7
agcttagtaa agccctcgct ag                                              22

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide

<400> SEQUENCE: 8
ttacgtaccc agcaaaggga gcaagtaatg aacaac                               36

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide

<400> SEQUENCE: 9
aagatcttct tagcgggcgg cttcgtatat ac                                   32

<210> SEQ ID NO 10
<211> LENGTH: 100
<212> TYPE: DNA
<213> ORGANISM: Artificial Sequence
<220> FEATURE:
<223> OTHER INFORMATION: Oligonucleotide

<400> SEQUENCE: 10
gtcaggagta ttatcgtgat tagtctattc gacatgttta aggtggggat tggtccctca     60
tcttcccata ccgtagggcc tgtaggctgg agctgcttcg                          100

<210> SEQ ID NO 11
<211> LENGTH: 103
<212> TYPE: DNA
<213> ORGANISM: Artificial Sequence
<220> FEATURE:
<223> OTHER INFORMATION: Oligonucleotide

<400> SEQUENCE: 11
gggcgagtaa gaagtattag tcacactgga ctttgattgc cagaccaccg cgtgaggttt     60
cgcggtattt ggcgttcatg tcccatatga atatcctcct aag                      103

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
cagcgttcga ttcatctgcg                                                 20

<210> SEQ ID NO 13
<211> LENGTH: 20
<212> TYPE: DNA
<213> ORGANISM: Artificial Sequence
```

```
<220> FEATURE:
<223> OTHER INFORMATION: Oligonucleotide

<400> SEQUENCE: 13
gaccaatcag cggaagcaag                                                     20

<210> SEQ ID NO 14
<211> LENGTH: 98
<212> TYPE: DNA
<213> ORGANISM: Artificial Sequence
<220> FEATURE:
<223> OTHER INFORMATION: Oligonucleotide

<400> SEQUENCE: 14
cggcattggc ccttccagtt ctcataccgt tggaccaatg aaagcgggta aacaatttac         60
cgacgatctg attgcccgtg taggctggag ctgcttcg                                 98

<210> SEQ ID NO 15
<211> LENGTH: 100
<212> TYPE: DNA
<213> ORGANISM: Artificial Sequence
<220> FEATURE:
<223> OTHER INFORMATION: Oligonucleotide

<400> SEQUENCE: 15
cgcaggcaac gatcttcatt gccaggccgc cgcgagaggt ttcgcggtac ttggcgttca         60
tatctttacc tgtttcgtac catatgaata tcctccttag                              100

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide

<400> SEQUENCE: 16
gcgtaagtac agcggtcac                                                      19

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide

<400> SEQUENCE: 17
cgatgccgga acaggctacg gc                                                  22

<210> SEQ ID NO 18
<211> LENGTH: 98
<212> TYPE: DNA
<213> ORGANISM: Artificial Sequence
<220> FEATURE:
<223> OTHER INFORMATION: Oligonucleotide

<400> SEQUENCE: 18
cccatccttc tcaacttaaa gactaagact gtcatgaaaa agaccaaaat tgtttgcacc         60
atcggaccga aaaccgaatg taggctggag ctgcttcg                                 98

<210> SEQ ID NO 19
<211> LENGTH: 99
<212> TYPE: DNA
<213> ORGANISM: Artificial Sequence
<220> FEATURE:
```

<223> OTHER INFORMATION: Oligonucleotide

<400> SEQUENCE: 19
ggacgtgaac agatgcggtg ttagtagtgc cgctcggtac cagtgcacca gaaaccataa    60
ctacaacgtc acctttgtgc atatgaatat cctccttag                           99

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide

<400> SEQUENCE: 20
gcgtaacctt ttccctggaa cg                                             22

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide

<400> SEQUENCE: 21
gcgttgctgg agcaacctgc cagc                                           24

<210> SEQ ID NO 22
<211> LENGTH: 125
<212> TYPE: DNA
<213> ORGANISM: Artificial Sequence
<220> FEATURE:
<223> OTHER INFORMATION: Oligonucleotide

<400> SEQUENCE: 22
ccactgactt tcgccatgac gaaccagaac cagcttagtt acagccataa tatacctcct    60
tattccacac agtatacgag ccggatgatt aatcgccaac agctctgtag gctggagctg   120
cttcg                                                               125

<210> SEQ ID NO 23
<211> LENGTH: 105
<212> TYPE: DNA
<213> ORGANISM: Artificial Sequence
<220> FEATURE:
<223> OTHER INFORMATION: Oligonucleotide

<400> SEQUENCE: 23
ggttatgcgt aagcattgct gttgcttcgt cgcggcaata taatgagaat tattatcatt    60
aaaagatgat tgaggagta agtatcatat gaatatcctc cttag                    105

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide

<400> SEQUENCE: 24
ccttcctctt tcagcagctt acc                                            23

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide

<400> SEQUENCE: 25
cgacgatcag cgcaaagtga aagg                                              24

<210> SEQ ID NO 26
<211> LENGTH: 126
<212> TYPE: DNA
<213> ORGANISM: Artificial Sequence
<220> FEATURE:
<223> OTHER INFORMATION: Oligonucleotide

<400> SEQUENCE: 26
cggcgttcca ctgcgtttca ccgtggcgga ctaggtatac ctgtaacata atatacctcc       60
ttattccaca cagtatacga gccggatgat taatcgccaa cagctctgta ggctggagct      120
gcttcg                                                                126

<210> SEQ ID NO 27
<211> LENGTH: 106
<212> TYPE: DNA
<213> ORGANISM: Artificial Sequence
<220> FEATURE:
<223> OTHER INFORMATION: Oligonucleotide

<400> SEQUENCE: 27
gcgggattgg tggtcgcaca gacaacttgg tgcataatca gcattactca gaaaattaac       60
gttacagcag tatacggaaa aaaagccata tgaatatcct ccttag                    106

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide

<400> SEQUENCE: 28
ccttacgacc aatctcatca ataccgg                                           27

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide

<400> SEQUENCE: 29
gcaataccat gactcaccag c                                                 21

<210> SEQ ID NO 30
<211> LENGTH: 100
<212> TYPE: DNA
<213> ORGANISM: Artificial Sequence
<220> FEATURE:
<223> OTHER INFORMATION: Oligonucleotide

<400> SEQUENCE: 30
ttcgtgtgcc ggacgagcta cccgccgtca atttcttgcg tgaagaaaac gtctttgtga       60
tgacaacttc tcgtgcgtct tgtaggctgg agctgcttcg                            100

<210> SEQ ID NO 31
<211> LENGTH: 100
<212> TYPE: DNA

<210> SEQ ID NO 31
<211> LENGTH: 100
<212> TYPE: DNA
<213> ORGANISM: Artificial Sequence
<220> FEATURE:
<223> OTHER INFORMATION: Oligonucleotide

<400> SEQUENCE: 31
atccagcgtt ggattcatgt gccgtagatc gtatggcgtg atctggtaga cgtaatagtt    60
gagccagttg gtaaacagta catatgaata tcctccttag                          100

<210> SEQ ID NO 32
<211> LENGTH: 30
<212> TYPE: DNA
<213> ORGANISM: Artificial Sequence
<220> FEATURE:
<223> OTHER INFORMATION: Oligonucleotide

<400> SEQUENCE: 32
tcaccttcaa catgcaggct cgacattggc                                     30

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide

<400> SEQUENCE: 33
ataaaaaagg cacccgaagg tgcctgaggt                                     30

<210> SEQ ID NO 34
<211> LENGTH: 99
<212> TYPE: DNA
<213> ORGANISM: Artificial Sequence
<220> FEATURE:
<223> OTHER INFORMATION: Oligonucleotide

<400> SEQUENCE: 34
gccccggctt ccagtgccaa tatgagcgtc gggtttgatg tgctcggggc ggcggtgaca    60
cctgttgatg gtgcattgct gtaggctgga gctgcttcg                           99

<210> SEQ ID NO 35
<211> LENGTH: 97
<212> TYPE: DNA
<213> ORGANISM: Artificial Sequence
<220> FEATURE:
<223> OTHER INFORMATION: Oligonucleotide

<400> SEQUENCE: 35
ccgccgtatc cagccggcaa atatgaacaa aaccttcctg attttgcagg tagttcttac    60
ccaaccagtc ggcaacgcat atgaatatcc tccttag                             97

<210> SEQ ID NO 36
<211> LENGTH: 22
<212> TYPE: DNA
<213> ORGANISM: Artificial Sequence
<220> FEATURE:
<223> OTHER INFORMATION: Oligonucleotide

<400> SEQUENCE: 36
gccgcgcgcg tggcgaaggc cc                                             22

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide

<400> SEQUENCE: 37
ggcgaccgga gccgggaagg c                                      21

<210> SEQ ID NO 38
<211> LENGTH: 40
<212> TYPE: DNA
<213> ORGANISM: Artificial Sequence
<220> FEATURE:
<223> OTHER INFORMATION: Oligonucleotide

<400> SEQUENCE: 38
ttatcatgag agtgttgaag ttcggcggta catcagtggc                   40

<210> SEQ ID NO 39
<211> LENGTH: 39
<212> TYPE: DNA
<213> ORGANISM: Artificial Sequence
<220> FEATURE:
<223> OTHER INFORMATION: Oligonucleotide

<400> SEQUENCE: 39
ttacccgggc cgccgccccg agcacatcaa acccgacgc                    39

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide

<400> SEQUENCE: 40
ccgacagtaa gacgggtaag cctg                                    24

<210> SEQ ID NO 41
<211> LENGTH: 22
<212> TYPE: DNA
<213> ORGANISM: Artificial Sequence
<220> FEATURE:
<223> OTHER INFORMATION: Oligonucleotide

<400> SEQUENCE: 41
agcttagtaa agccctcgct ag                                      22

<210> SEQ ID NO 42
<211> LENGTH: 57
<212> TYPE: DNA
<213> ORGANISM: Artificial Sequence
<220> FEATURE:
<223> OTHER INFORMATION: Oligonucleotide

<400> SEQUENCE: 42
cgtatttccg tggtgctgat tacgcaattc tcttccgagt actcaatcag tttctgc    57

<210> SEQ ID NO 43
<211> LENGTH: 57
<212> TYPE: DNA
<213> ORGANISM: Artificial Sequence
<220> FEATURE:
<223> OTHER INFORMATION: Oligonucleotide

<400> SEQUENCE: 43
gcagaaactg attgagtact cggaagagaa ttgcgtaatc agcaccacgg aaatacg    57

<210> SEQ ID NO 44
<211> LENGTH: 50
<212> TYPE: DNA
<213> ORGANISM: Artificial Sequence
<220> FEATURE:
<223> OTHER INFORMATION: Oligonucleotide

<400> SEQUENCE: 44
cgtagttaac gaattcccaa ctagttgcat catacaacta ataaacgtgg        50

<210> SEQ ID NO 45
<211> LENGTH: 90
<212> TYPE: DNA
<213> ORGANISM: Artificial Sequence
<220> FEATURE:
<223> OTHER INFORMATION: Oligonucleotide

<400> SEQUENCE: 45 cccggggag gcgcccgcgg atcccggtat accagaaagg cccacccgaa ggtgagccag        60
gaaggtaacc agttcagaag ctgctatcag        90

<210> SEQ ID NO 46
<211> LENGTH: 91
<212> TYPE: DNA
<213> ORGANISM: Artificial Sequence
<220> FEATURE:
<223> OTHER INFORMATION: Oligonucleotide

<400> SEQUENCE: 46
tcctggctca ccttcgggtg ggcctttctg gtataccggg atccgcgggc gcctcccccg        60
ggaatctatt cattatctca atcaggccgg g        91

<210> SEQ ID NO 47
<211> LENGTH: 40
<212> TYPE: DNA
<213> ORGANISM: Artificial Sequence
<220> FEATURE:
<223> OTHER INFORMATION: Oligonucleotide

<400> SEQUENCE: 47
cgtagttaac gaattcgaga atgcccgagg gaaagatctg        40

<210> SEQ ID NO 48
<211> LENGTH: 29
<212> TYPE: DNA
<213> ORGANISM: Artificial Sequence
<220> FEATURE:
<223> OTHER INFORMATION: Oligonucleotide

<400> SEQUENCE: 48
ggggtatact gtaggctgga gctgcttcg        29

<210> SEQ ID NO 49
<211> LENGTH: 29
<212> TYPE: DNA
<213> ORGANISM: Artificial Sequence
<220> FEATURE:
<223> OTHER INFORMATION: Oligonucleotide

<400> SEQUENCE: 49
cgcggatccc atatgaatat cctccttag        29

<210> SEQ ID NO 50
<211> LENGTH: 22

<212> TYPE: DNA
<213> ORGANISM: Artificial Sequence
<220> FEATURE:
<223> OTHER INFORMATION: Oligonucleotide

<400> SEQUENCE: 50
cgtgttgcgt gttaccaact cg                                    22

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide

<400> SEQUENCE: 51
cggaaactga cgcctccgca g                                     21

<210> SEQ ID NO 52
<211> LENGTH: 100
<212> TYPE: DNA
<213> ORGANISM: Artificial Sequence
<220> FEATURE:
<223> OTHER INFORMATION: Oligonucleotide

<400> SEQUENCE: 52
ctggctttca caaggccgta tggcgagcag gagaagcaaa ttcttactgc cgaagcggta    60
gaatttctga ctgagctggt tgtaggctgg agctgcttcg                         100

<210> SEQ ID NO 53
<211> LENGTH: 99
<212> TYPE: DNA
<213> ORGANISM: Artificial Sequence
<220> FEATURE:
<223> OTHER INFORMATION: Oligonucleotide

<400> SEQUENCE: 53
aacatcttcc acatgcccctt cacgtatgcg gttttgtagt gcgcgccagt aatcagcgcg    60
gaacaggtcg gcgtgcatcc atatgaatat cctccttag                          99

<210> SEQ ID NO 54
<211> LENGTH: 24
<212> TYPE: DNA
<213> ORGANISM: Artificial Sequence
<220> FEATURE:
<223> OTHER INFORMATION: Oligonucleotide

<400> SEQUENCE: 54
cgttaagcga ttcagcacct tacc                                  24

<210> SEQ ID NO 55
<211> LENGTH: 27
<212> TYPE: DNA
<213> ORGANISM: Artificial Sequence
<220> FEATURE:
<223> OTHER INFORMATION: Oligonucleotide

<400> SEQUENCE: 55
aacgcattac ccactctgtt taatacg                               27

<210> SEQ ID NO 56
<211> LENGTH: 100
<212> TYPE: DNA
<213> ORGANISM: Artificial Sequence
<220> FEATURE:

```
<223> OTHER INFORMATION: Oligonucleotide

<400> SEQUENCE: 56
tttttgcccg ctatggctta ccagcaccgg tgggttatgc ctgtactact ccgcgcgaag    60
cagaagaagc cgcttcaaaa catatgaata tcctccttag                          100

<210> SEQ ID NO 57
<211> LENGTH: 100
<212> TYPE: DNA
<213> ORGANISM: Artificial Sequence
<220> FEATURE:
<223> OTHER INFORMATION: Oligonucleotide

<400> SEQUENCE: 57
atatccgcca ggctgcgaac ggttttcacg cctgcggctt ccagagcagc gaatttctca    60
tccgcagtcc ctttaccggc tgtaggctgg agctgcttcg                          100

<210> SEQ ID NO 58
<211> LENGTH: 28
<212> TYPE: DNA
<213> ORGANISM: Artificial Sequence
<220> FEATURE:
<223> OTHER INFORMATION: Oligonucleotide

<400> SEQUENCE: 58
tcgcgaatcc gtgggcttcc tggtaacg                                       28

<210> SEQ ID NO 59
<211> LENGTH: 29
<212> TYPE: DNA
<213> ORGANISM: Artificial Sequence
<220> FEATURE:
<223> OTHER INFORMATION: Oligonucleotide

<400> SEQUENCE: 59
cctctgatgc caaccgaaga gatgagccg                                      29

<210> SEQ ID NO 60
<211> LENGTH: 97
<212> TYPE: DNA
<213> ORGANISM: Artificial Sequence
<220> FEATURE:
<223> OTHER INFORMATION: Oligonucleotide

<400> SEQUENCE: 60
cccgcacatt cttatcgttg aagacgagtt ggtaacacgc aacacgttga aaagtatttt    60
cgaagcggaa ggctatgtgt aggctggagc tgcttcg                             97

<210> SEQ ID NO 61
<211> LENGTH: 99
<212> TYPE: DNA
<213> ORGANISM: Artificial Sequence
<220> FEATURE:
<223> OTHER INFORMATION: Oligonucleotide

<400> SEQUENCE: 61
ccagatcacc gcagaagcga taaccttcac cgtgaatggt ggcgatgatt tccggcgtat    60
ccggcgtaga ttcgaaatgc atatgaatat cctccttag                           99

<210> SEQ ID NO 62
<211> LENGTH: 20
<212> TYPE: DNA
<213> ORGANISM: Artificial Sequence
```

<220> FEATURE:
<223> OTHER INFORMATION: Oligonucleotide

<400> SEQUENCE: 62
cgacaattgg attcaccacg                                                    20

<210> SEQ ID NO 63
<211> LENGTH: 21
<212> TYPE: DNA
<213> ORGANISM: Artificial Sequence
<220> FEATURE:
<223> OTHER INFORMATION: Oligonucleotide

<400> SEQUENCE: 63
gcggtattga aaggttggtg c                                                  21

<210> SEQ ID NO 64
<211> LENGTH: 70
<212> TYPE: DNA
<213> ORGANISM: Artificial Sequence
<220> FEATURE:
<223> OTHER INFORMATION: Oligonucleotide

<400> SEQUENCE: 64
taaacaacat aagcacaatc gtattaatat ataagggttt tatatctatg tgtaggctgg        60
agctgcttcg                                                               70

<210> SEQ ID NO 65
<211> LENGTH: 70
<212> TYPE: DNA
<213> ORGANISM: Artificial Sequence
<220> FEATURE:
<223> OTHER INFORMATION: Oligonucleotide

<400> SEQUENCE: 65
taagcgtagc gccatcaggc atttacaact taaatcacac cctgcgccag catatgaata        60
tcctccttag                                                               70

<210> SEQ ID NO 66
<211> LENGTH: 21
<212> TYPE: DNA
<213> ORGANISM: Artificial Sequence
<220> FEATURE:
<223> OTHER INFORMATION: Oligonucleotide

<400> SEQUENCE: 66
ccttaacgtt attgtctctg c                                                  21

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
ggaggaagcc ccagagcagg                                                    20

<210> SEQ ID NO 68
<211> LENGTH: 125
<212> TYPE: DNA
<213> ORGANISM: Artificial Sequence
<220> FEATURE:
<223> OTHER INFORMATION: Oligonucleotide

<400> SEQUENCE: 68
ggtaccggat ccgggcccga gctgttgaca attaatcatc cggctcgtat aatgtgtgga    60
attgtgagcg gataacaatt tacgtataag gaggtatatt atgaaagtta caaatcaaaa   120
agaac                                                              125

<210> SEQ ID NO 69
<211> LENGTH: 124
<212> TYPE: DNA
<213> ORGANISM: Artificial Sequence
<220> FEATURE:
<223> OTHER INFORMATION: Oligonucleotide

<400> SEQUENCE: 69
gagctcaagc ttaacagata aaacgaaagg cccagtcttt cgactgagcc tttcgtttta    60
tttgatgcct agggctagct ctagattaat taaaatgatt ttatatagat atccttaagt   120
tcac                                                               124

<210> SEQ ID NO 70
<211> LENGTH: 35
<212> TYPE: DNA
<213> ORGANISM: Artificial Sequence
<220> FEATURE:
<223> OTHER INFORMATION: Oligonucleotide

<400> SEQUENCE: 70
tctagaggat ccaagttcaa caggagagca ttatg                              35

<210> SEQ ID NO 71
<211> LENGTH: 44
<212> TYPE: DNA
<213> ORGANISM: Artificial Sequence
<220> FEATURE:
<223> OTHER INFORMATION: Oligonucleotide

<400> SEQUENCE: 71
ggatccgcta gccctaggta cgtactactc ttccatcgcc tggc                    44

<210> SEQ ID NO 72
<211> LENGTH: 62
<212> TYPE: DNA
<213> ORGANISM: Artificial Sequence
<220> FEATURE:
<223> OTHER INFORMATION: Oligonucleotide

<400> SEQUENCE: 72
agctgtatac tagaattcat agatcttaag gaggtatatt atggaatacc gtagcctgac    60
gc                                                                  62

<210> SEQ ID NO 73
<211> LENGTH: 129
<212> TYPE: DNA
<213> ORGANISM: Artificial Sequence
<220> FEATURE:
<223> OTHER INFORMATION: Oligonucleotide

<400> SEQUENCE: 73
gcttataagc cagctggctc tagatagcag aaaggcccac cgaaggtga gccaggagta    60 tacatgaagc atttccgtta attaacggag ctcatcctag gtcagggttt cacaccaatt   120
tgcagcgcc                                                          129

<210> SEQ ID NO 74
<211> LENGTH: 31
<212> TYPE: DNA
<213> ORGANISM: Artificial Sequence
<220> FEATURE:
<223> OTHER INFORMATION: Oligonucleotide

<400> SEQUENCE: 74
ctagtctaga ttagtacagc agacgggcgc g         31

<210> SEQ ID NO 75
<211> LENGTH: 35
<212> TYPE: DNA
<213> ORGANISM: Artificial Sequence
<220> FEATURE:
<223> OTHER INFORMATION: Oligonucleotide

<400> SEQUENCE: 75
tcccccggga agcttccgtc agggcgtggt gaccg         35

<210> SEQ ID NO 76
<211> LENGTH: 39
<212> TYPE: DNA
<213> ORGANISM: Artificial Sequence
<220> FEATURE:
<223> OTHER INFORMATION: Oligonucleotide

<400> SEQUENCE: 76
cccaagcttt gacttctatg tataccgtgg gtgattatc         39

<210> SEQ ID NO 77
<211> LENGTH: 265
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t

<400> SEQUENCE: 77
ggaattctta gcttttattc tgttcggcga acagyhddna artcasncat gaacaacttt         60
aatctgcaca ccccaacccg cattctgttt ggtaaaggcg caatcgctgg tttacgcgaa        120
caaattccgt gtaggctgga gctgcttcgy hdrdnaartc asncttagcg ggcggcttcg        180
tatatacggc ggctgacatc caacgtaatg tcatgatttt cgcccagttg ggtcatgccg        240
tgctccatat gaatatcctc cttag        265

<210> SEQ ID NO 78
<211> LENGTH: 101
<212> TYPE: DNA
<213> ORGANISM: Artificial Sequence
<220> FEATURE:
<223> OTHER INFORMATION: Oligonucleotide

<400> SEQUENCE: 78
atgaacaact ttaatctgca cacccaacc cgcattctgt ttggtaaagg cgcaatcgct    60
ggtttacgcg aacaaattcc gtgtaggctg gagctgcttc g                      101

<210> SEQ ID NO 79
<211> LENGTH: 101
<212> TYPE: DNA
<213> ORGANISM: Artificial Sequence
<220> FEATURE:
<223> OTHER INFORMATION: Oligonucleotide

<400> SEQUENCE: 79
ttagcgggcg gcttcgtata tacggcggct gacatccaac gtaatgtcat gattttcgcc    60
cagttgggtc atgccgtgct ccatatgaat atcctcctta g                       101

<210> SEQ ID NO 80
<211> LENGTH: 33
<212> TYPE: DNA
<213> ORGANISM: Artificial Sequence
<220> FEATURE:
<223> OTHER INFORMATION: Oligonucleotide

<400> SEQUENCE: 80
ggcgtctcgc catacaacaa acgcacatcg ggc                                33

<210> SEQ ID NO 81
<211> LENGTH: 29
<212> TYPE: DNA
<213> ORGANISM: Artificial Sequence
<220> FEATURE:
<223> OTHER INFORMATION: Oligonucleotide

<400> SEQUENCE: 81
gggctttgcc gacaccttct tcgttcttg                                     29

<210> SEQ ID NO 82
<211> LENGTH: 43
<212> TYPE: DNA
<213> ORGANISM: Artificial Sequence
<220> FEATURE:
<223> OTHER INFORMATION: Oligonucleotide

<400> SEQUENCE: 82
cgatgcacgt catgaacaac tttaatctgc acccccaac ccg                      43

<210> SEQ ID NO 83
<211> LENGTH: 70
<212> TYPE: DNA
<213> ORGANISM: Artificial Sequence
<220> FEATURE:
<223> OTHER INFORMATION: Oligonucleotide

<400> SEQUENCE: 83
ggcgtaaaaa gcttagcggg cggcttcgta tatacggcgg ctgacatcca acgtaatgtc    60
gtgattttcg                                                          70

<210> SEQ ID NO 84
<211> LENGTH: 40
<212> TYPE: DNA
<213> ORGANISM: Artificial Sequence
<220> FEATURE:
<223> OTHER INFORMATION: Oligonucleotide

<400> SEQUENCE: 84

```
cccaagcttt gatggctcaa atcttcaatt ttagttctgg                         40
```

<210> SEQ ID NO 85
<211> LENGTH: 35
<212> TYPE: DNA
<213> ORGANISM: Artificial Sequence
<220> FEATURE:
<223> OTHER INFORMATION: Oligonucleotide

<400> SEQUENCE: 85

```
ggaattctta accgtgacgg cgttcgaact caacc                              35
```

<210> SEQ ID NO 86
<211> LENGTH: 37
<212> TYPE: DNA
<213> ORGANISM: Artificial Sequence
<220> FEATURE:
<223> OTHER INFORMATION: Oligonucleotide

<400> SEQUENCE: 86

```
cccaagcttt gatgggattg actactaaac ctctatc                            37
```

<210> SEQ ID NO 87
<211> LENGTH: 34
<212> TYPE: DNA
<213> ORGANISM: Artificial Sequence
<220> FEATURE:
<223> OTHER INFORMATION: Oligonucleotide

<400> SEQUENCE: 87

```
gggatcctta ccatttcaac agatcgtcct tagc                               34
```

<210> SEQ ID NO 88
<211> LENGTH: 122
<212> TYPE: DNA
<213> ORGANISM: Artificial Sequence
<220> FEATURE:
<223> OTHER INFORMATION: Oligonucleotide

<400> SEQUENCE: 88

```
cgggcaatat gtctctgtgt ggattaaaaa aagagtgtct gatagcagct tctgaactgg   60
ttaccttcct ggctcacctt cgggtgggcc tttctggtat actgtaggct ggagctgctt   120
cg                                                                 122
```

<210> SEQ ID NO 89
<211> LENGTH: 130
<212> TYPE: DNA
<213> ORGANISM: Artificial Sequence
<220> FEATURE:
<223> OTHER INFORMATION: Oligonucleotide

<400> SEQUENCE: 89

```
ccctgtcatt tttctccata atttcttcat aaaaaagccg gctgcataa aagcaaaccc    60 ggcctgattg agataatgaa tagattcccg ggggaggcgc ccgcggatcc catatgaata   120
tcctccttag                                                         130
```

<210> SEQ ID NO 90
<211> LENGTH: 27
<212> TYPE: DNA
<213> ORGANISM: Artificial Sequence
<220> FEATURE:
<223> OTHER INFORMATION: Oligonucleotide

```
<400> SEQUENCE: 90
gccatgccgc gctggtgttt ggtcgcg                                         27

<210> SEQ ID NO 91
<211> LENGTH: 24
<212> TYPE: DNA
<213> ORGANISM: Artificial Sequence
<220> FEATURE:
<223> OTHER INFORMATION: Oligonucleotide

<400> SEQUENCE: 91
gcgaccagaa ccagggaaag tgcg                                            24

<210> SEQ ID NO 92
<211> LENGTH: 35
<212> TYPE: DNA
<213> ORGANISM: Artificial Sequence
<220> FEATURE:
<223> OTHER INFORMATION: Oligonucleotide

<400> SEQUENCE: 92
tgctctagag tccgcgctgt gcaaatccag aatgg                                35

<210> SEQ ID NO 93
<211> LENGTH: 34
<212> TYPE: DNA
<213> ORGANISM: Artificial Sequence
<220> FEATURE:
<223> OTHER INFORMATION: Oligonucleotide

<400> SEQUENCE: 93
cccaagctta actctctaca acagaaataa aaac                                 34

<210> SEQ ID NO 94
<211> LENGTH: 104
<212> TYPE: DNA
<213> ORGANISM: Artificial Sequence
<220> FEATURE:
<223> OTHER INFORMATION: Oligonucleotide

<400> SEQUENCE: 94
agaactagtg agctgttgac aattaatcat ccggctcgta taatgtgtgg aagtcgacgg     60
atcctaagga ggttataaat gaacaacttt aatctgcaca cccc                     104

<210> SEQ ID NO 95
<211> LENGTH: 86
<212> TYPE: DNA
<213> ORGANISM: Artificial Sequence
<220> FEATURE:
<223> OTHER INFORMATION: Oligonucleotide

<400> SEQUENCE: 95
gagcccgggg cagaaaggcc cacccgaagg tgagccagtg tgatacgtag aattcttaat     60
taagttagct tttattctgt tcggcg                                          86
```